United States Patent [19]
Chao

[11] Patent Number: 5,648,997
[45] Date of Patent: Jul. 15, 1997

[54] APPARATUS AND METHOD FOR REMOVING SCATTER FROM AN X-RAY IMAGE

[75] Inventor: Yong-Sheng Chao, Storrs, Conn.

[73] Assignee: Advanced Optical Technologies, Inc., East Hartford, Conn.

[21] Appl. No.: 580,602

[22] Filed: Dec. 29, 1995

[51] Int. Cl.$^6$ ...................................................... H05G 1/64
[52] U.S. Cl. ...................... 378/98.4; 378/98.12; 378/147
[58] Field of Search ................................ 378/98.11, 984, 378/98.12, 98.2, 98.9, 901, 4, 147, 149, 154, 19, 62

[56] References Cited

U.S. PATENT DOCUMENTS

| 4,792,900 | 12/1988 | Sones et al. | 378/98.8 |
| 5,148,455 | 9/1992 | Stein | 378/55 |

OTHER PUBLICATIONS

Lehmann et al., *Generalized Image Combinations in Dual KVP Digital Radiography*, 8 Medical Physics 659 (Sep./Oct. 1981).

Archer et al., *A Laplace Transform Pair Model for Spectral Reconstruction*, 9 Medical Physics 844 Nov./Dec. 1982).

Speller et al., *Monte Carlo Study of Multiple Scatter Effects in Compton Scatter Sitometry*, 15 Medical Physics 707 (Sep./Oct. 1988).

Boone et al., *Monte Carlo Simulation of the Scattered Radiation Distribution in Diagnostic Radiology*, 15 Medical Physics 713 (Sep./Oct. 1988).

Boone et al., *An Analytical Model of the Scattered Radiation Distribution in Diagnostic Radiology*, 15 Medical Physics 721 (Sep./Oct. 1988).

Vetter et al., *Correction for Scattered Radiation and Other Background Signals in Dual–Energy Computed Tomography Material Thickness Measurements*, Medical Physics 726 (Sep./Oct. 1988).

Wagner et al., *Dual–Energy X–Ray Projection Imaging: Two Sampling Schemes for the Correction of Scattered Radiation*, 15 Medical Physics 732 (Sep./Oct. 1988).

Archer et al., *Laplace Reconstruction of Experimental Diagnostic X–Ray Spectra*, 15 Medical Physics 832 (Nov./Dec. 1988).

Cardinal et al., *An Accurate Method for Direct Dual–Energy Calibration and Decomposition*, 17 Medical Physics 327 (May/Jun. 1990).

Chan et al., *Studies of Performance of Aniscatter Grids in Digital Radiography: Effects on Signal–to–Noise Ratio*, 17 Medical Physics 655 (Jul./Aug. 1990).

Honda et al., *Method for Estimating the Intensity of Scattered Radiation Using a Scatter Generation Model*, 18 Medical Physics 219 (Mar./Apr. 1991).

(List continued on next page.)

*Primary Examiner*—Don Wong
*Attorney, Agent, or Firm*—Morse, Altman & Benson

[57] ABSTRACT

An apparatus, for producing scatter-free two-dimensional X-ray images and eliminating scattering effects on integrated detector arrays, includes, in physical sequence from front to back, an X-ray source, a front two-dimensional detector positioned behind a subject for detecting both primary and scatter X-rays produced from striking the subject with the source's radiation, a collimator with holes for passing a portion of the primary X-rays, and a rear two-dimensional detector for receiving this portion. A method for producing scatter-free images which includes the steps of; X-raying the subject with high and low energy, retrieving an image pair $I_{rHl}$ and $I_{rLl}$ from the rear detector, normalizing and subtracting dark signals from $I_{rHl}$ and $I_{rLl}$ to yield an image pair $D_{rHl}$ and $D_{rLl}$, solving $D_{rHl}$ and $D_{rLl}$ to determine b and s, retrieving an image $I_{fh}$ from the front detector, normalizing and subtracting dark signals from $I_{fh}$ to yield $D_{fh}$ representing the primary and scatter X-rays sum, determining $D_{fSl}$ of image $D_{fh}$ at the detector cells using b and s, interpolating $D_{fSl}$ for the front detector cells to yield $D_{fSh}$, subtracting $D_{fSh}$ from $D_{fh}$ to yield $D_{fPh}$ representing the two-dimensional scatter-free image of the subject.

37 Claims, 9 Drawing Sheets

OTHER PUBLICATIONS

Floyd et al., *Quanitative Scatter Measurement in Digital Radiography Using Photostimulable Phosphor Imaging System*, 18 Medical Physics 408 (May/Jun. 1991).

Antonuk et al., *Deomonstration of Megavoltage and Diagnostic X-Ray Imaging with Hydrogenated Amorphous Silicon Arrays*, 19 Medical Physics 1455 (Nov./Dec. 1992).

Honda et al., *A Technique of Scatter-Glare Correction Using Digital Filtration*, 20 Medical Physics 59 (Jan./Feb. 1993).

Zhao et al., *A Large Area Solid-State Detector for Radiology Unsing Amorphous Selenium*, 1651 SPIE Medical Imaging VI: Instrumentation 134 (1992).

Petrone et al., *Rare-Earth Scatter Fractions in Chest Radiography*, 20 Medical Physics 475 (Mar./Apr. 1993).

Wahner et al., *The Evaluation of Osteoporosis: Dual Energy X-Ray Absorptiometry in Clinical Practice* 14–33 (1994).

Lee et al., *A New Digital Detector for Projection Radiography*, SPIE (Feb. 1995).

Chuang et al., *Comparison of Four Dual Energy Image Decomposition Methods*, 4 Physics in Medicine and Biology 455 (1988).

Seibert et al., *X-Ray Scatter Removal by Deconvolution*, 15 Medical Physics 567 (Jul./Aug. 1988).

Zhao et al., *Digital Radiology Using Self-scanned Readout of Amorphous Selenium*, 1896 SPIE Physics of Medical Imaging 114 (1993).

APPARATUS AND METHOD FOR REMOVING SCATTER FROM AN X-RAY IMAGE

GOVERNMENT FUNDING

The research involved in this application was funded in part by the National Aeronautics and Space Administration, contract number NAS 9-19061. The intellectual property rights of the applicant and the government of the United States of America are governed by Title 37 Code of Federal Regulations Part 401.

BACKGROUND OF THE INVENTION

1. Field of the Invention

This invention relates generally to digital x-ray imaging and, more particularly, relates to methods and apparatuses for reducing scatter in two-dimensional x-ray imaging and two-dimensional dual-energy x-ray imaging.

2. The Prior Art

Recent advances in the field of semiconductor fabrication have resulted in the ability to fabricate large-format two-dimensional integrated detector arrays for x-ray detection. These arrays have on the order of one million detector cells and provide instant acquisition of two-dimensional x-ray images with exceedingly high quality.

Scatter, which results from those x-rays that strike objects and deflect in random directions, has been a difficult and on-going problem in x-ray imaging using two-dimensional detectors. For example, in projection chest radiography, scatter typically accounts for between approximately 30% and 50% of the total amount of x-rays detected.

With single-point detectors or linear detector arrays, because of the inherent geometric configuration of the detector, scatter can be controlled so that its effects are negligible. However, two-dimensional detectors are exposed to wide-angle random scatter. Randomly scattered x-rays are superimposed on the primary x-rays (the x-rays coming directly from the x-ray source) and recorded by two-dimensional detectors undifferentiated, degrading the true image. Scatter tends to reduce image contrast, produce blurring, and reduce signal-to-noise ratio. Furthermore, if scatter is not substantially reduced, almost all quantitative digital x-ray imaging using two-dimensional detector arrays becomes meaningless. For example, currently, dual-energy x-ray imaging, which is a method for determining two material composition images of a subject, can only be conducted using point or linear detector array scanning to gain a two-dimensional image. So, unless scatter is substantially removed or eliminated, two-dimensional detector arrays cannot be used in dual-energy x-ray imaging.

According to current theory and empirically derived data, a large number of complex material systems can be decomposed into only two basis material compositions in terms of x-ray absorption. In the case of the human body, these two materials are bone tissue and soft tissue, abbreviated b and s, respectively. The prior art of data decomposition methods is summarized in Keh-Shih Chung & H. K. Huang, *Comparison of Four Dual-energy Image Decomposition Methods*, 4 Physics in Medicine and Biology 455 (1988), and in the book Heinz W. Wahner & Ignac Fogelman, *The Evaluation of Osteoporosis: Dual-energy X-ray Absorptiometery in Clinical Practice* 14-33 (1994). All the data decomposition methods of the prior art have a common approach. They all use two single-energy values to replace the broad spectrum x-ray energy: the average energy $E_H$ for high-energy x-rays and the average energy $E_L$ for low-energy x-rays. Thus, the dual-energy equations are greatly simplified into a pair of linear algebraic equations that can be readily solved for b and s:

$$I_H = I_{HO} \times \exp(-(\mu_b(E_H) \times b + \mu_s(E_H) \times s)) \qquad (1a)$$

$$I_L = I_{LO} \times \exp(-(\mu_b(E_L) \times b + \mu_s(E_L) \times s)) \qquad (1b)$$

where $I_{HO}$ and $I_{LO}$ are the incident x-ray beam intensities at energies $E_H$ and $E_L$, respectively, $I_H$ and $I_L$ are the measured signals read from high-energy and low-energy detectors, respectively, $\mu_b(E_H)$ and $\mu_b(E_L)$ are the mass absorption coefficients of bone tissue of high-energy and low energy x-rays, respectively, and $\mu_s(E_H)$ and $\mu_s(E_L)$ are the mass absorption coefficients of soft tissue of high-energy and low energy x-rays, respectively. Taking the natural logarithm of equation pair (1a,1b) yields $$L_H = \ln(I_H/I_{HO}) = -(\mu_b(E_H) \times b + \mu_s(E_H) \times s) \qquad (2a)$$

$$L_L = \ln(I_L/I_{LO}) = -(\mu_b(E_L) \times b + \mu_s(E_L) \times s) \qquad (2b)$$

Thus, b and s can be analytically determined as simple functions of experimental data $L_H$ and $L_L$.

In most cases, because of so-called "beam hardening effects", the results directly calculated from the linearized equation pair (2a,2b) deviate too much from reality. Therefore, the results are subjected to numerous correction methods. These different correction methods account for the various data decomposition methods of the prior art. In some correction methods, the corrections extend to the second order. The data decomposition methods of prior art can be used in certain specific cases. For example, when measuring certain fixed points in the human body, the x-ray absorption varies only within a narrow range. However, for a human body with an average thickness of between 20 cm and 30 cm, the absorption of x-rays can vary greatly. The intensity can be being reduced by a small fraction of its incident intensity to as high as several hundred times. And the x-ray energy spectra as well as the average x-ray energy values change dramatically from one position to another. Thus, some inconsistencies arise from the linearization approach.

Currently, there are three basic methods for reducing scatter in two-dimensional x-ray imaging. The first method uses an anti-scatter grid to slightly relieve scatter effects on images. An anti-scatter grid consists of large number of fine wires placed in front of the detector. Because the grid has a certain amount of collimating ability, the randomly scattered x-rays can be somewhat reduced. However, the grid also tends to block the primary x-rays, causing distortion of the primary image. Thus, the grid must be thin, limiting its ability to reduce scatter. Recent research results show that up to about 50% of the scatter radiation can be reduced through use of an anti-scattering grid.

The second method to reduce scatter is to increase the air gap between the subject and the detector. The scatter is attenuated, but the image is blurred due to the geometric distance the x-rays have to travel.

The third method to reduce scatter is to calculate theoretical estimates of the amount of scatter and subtract these estimates from the detected image. Theoretical calculation methods, including Monte Carlo simulation methods and analytical deconvolution methods, can only give very crude predictions, and are not generally considered effective.

Thus, there continues to be a need to accurately remove scatter effects from images detected by large-format two-dimensional x-ray detector arrays and to produce scatter-free dual-energy x-ray images from these arrays.

SUMMARY OF THE INVENTION

The apparatus of the present invention includes: (a) in physical sequence from front to back, an x-ray source, a front two-dimensional x-ray detector assembly, a collimator, and a rear two-dimensional x-ray detector assembly, where the subject is located between the x-ray source and the front detector assembly; (b) the x-ray source adapted to emit x-rays for passage through the subject; (c) the x-rays including primary x-rays having their direction of travel unaltered by passing through the subject; (d) the x-rays including scatter x-rays having their direction of travel altered by interaction with the subject; (e) the front detector assembly receiving the primary x-rays and the scatter x-rays; (f) the collimator being adjacent to the front detector assembly, the collimator permitting the passage of a portion of the primary x-rays, completely blocking the passage of the remainder of the primary x-rays, and completely blocking the scatter x-rays; and (g) the rear detector assembly being adjacent to the collimator, the rear detector receiving only the portion of said primary x-rays passing through the collimator.

Preferably, the x-ray source emits x-rays with an energy in the range of from approximately 10 kiloelectron-volts (keV) to approximately 500 keV with a continuous x-ray spectrum, which is typical for medical diagnostic human body imaging. Preferably, the collimator is composed substantially of an x-ray-absorbent material having a large number of through holes, where the axes of the holes are parallel to the direction of travel of the primary x-rays and the holes have a substantially round cross-section with a diameter between approximately 0.5 millimeter (mm) and approximately 10 mm and a pitch of between approximately 2 mm and 50 mm.

In a first preferred embodiment of the apparatus, the x-ray source operates at a constant potential and emits a single pulse or a plurality of pulses at the same energy level, the rear detector assembly includes, in physical sequence from front to back, a rear low-energy detector array, a rear x-ray energy spectral filter, and a rear high-energy detector array, where the rear low-energy detector array includes a plurality of detector cells arranged in a substantially square matrix with from 32 to 8192 cells on a side, the rear high-energy detector array includes a plurality of detector cells, the arrangement and quantity of which are substantially the same as the arrangement and quantity of the rear low-energy detector cells.

In a second preferred embodiment of the apparatus, the x-ray source emits two temporally spaced pulses, a high-energy pulse and a low-energy pulse, the front detector assembly includes a plurality of detector cells arranged in a substantially square matrix with from 32 to 8192 cells on a side, and the rear detector array includes a plurality of detector cells arranged in a substantially square matrix with from 32 to 8192 cells on a side.

In a third preferred embodiment of the apparatus, the x-ray source operates at a constant potential and emits a single pulse or a plurality of pulses at the same energy level, the rear detector assembly includes, in physical sequence from front to back, a rear low-energy detector array, a rear x-ray energy spectral filter, and a rear high-energy detector array, where the rear low-energy detector array includes a plurality of detector cells arranged in a substantially square matrix with from 32 to 8192 cells on a side, the rear high-energy detector array includes a plurality of detector cells, the arrangement and quantity of which are substantially the same as the arrangement and quantity of the rear low-energy detector cells, and the front detector assembly includes, in physical sequence from front to back, a front low-energy detector array, a front x-ray energy spectral filter, and a front high-energy detector array, where the front low-energy detector array includes a plurality of detector cells arranged in a substantially square matrix with from 32 to 8192 cells on a side, the front high-energy detector array includes a plurality of detector cells, the arrangement and quantity of which are substantially the same as the arrangement and quantity of the front low-energy detector cells.

The basic methods of the present invention include a method for dual-energy x-ray data decomposition and a method for eliminating scatter. The method for dual-energy x-ray decomposition operates on a system including, in physical sequence from front to back, an x-ray source, a front two-dimensional x-ray detector assembly, a collimator with a plurality of holes, and a rear two-dimensional x-ray detector assembly, where the subject is located between the x-ray source and the front detector. Only the rear detector cells in a straight line from the x-ray source through the holes in the collimator receive an x-ray signal. This straight line is called a projection line. There is at least one projection line for each hole in the collimator. Some of the front detector cells are on a projection line and the remainder are not, but they all receive x-ray signals. A low-resolution image is the image represented by the composite of the detector cells on projection lines and a high-resolution image is the image represented by the composite of all the detector cells.

The dual-energy x-ray data decomposition method includes: (1) constructing a pair of numerical surface equations $D_H=D_H(b,s)$ and $D_L=D_L(b,s)$ for each detector assembly and saving them for later use, where H represents the high-energy x-ray signal and L represents the low-energy x-rays signal; (2) reconstructing a pair of numerical surface equations $b=b(D_H,D_L)$ and $s=s(D_H,D_L)$ by numerically inverting the equations of step 1 and saving them for later use; and (3) determining the desired values for b and s at each discrete cell location by inserting the available data pair $(D_H,D_L)$ into the numerical equations of step 2, or determining the desired values for $D_H$, $D_L$, or only one of them, at each discrete cell location by inserting the available data pair (b,s) into the numerical equations of step 1.

The method for eliminating scatter operates on the same apparatus as the method for dual-energy x-ray data decomposition, and includes (1) illuminating the subject with x-rays from the x-ray source, where the x-rays include high-energy x-rays (H) and low-energy x-rays (L); (2) retrieving a low-resolution image pair $I_{rHl}$ and $I_{rLl}$ from the rear detector assembly and processing them to normalize and to subtract dark signals, yielding a low-resolution image pair $D_{rHl}$ and $D_{rLl}$ that are functions of the subject materials; (3) solving the image pair $D_{rHl}$ and $D_{rLl}$ to determine the subject materials b and s; (4) retrieving a high-resolution image $I_{fn}$ from the front detector and processing it to normalize and to subtract dark signals, yielding a high-resolution image $D_{fn}$, which is the sum of primary x-rays and scatter x-rays; (5) determining the low-resolution scatter component $D_{fsl}$ of image $D_{fn}$ at the detector cells on projection lines by inserting the values for b and s and solving for $D_{fsl}$; and (6) interpolating $D_{fsl}$ for those front detector cells not on the projection lines, yielding the high-resolution scatter image $D_{fsh}$, and subtracting $D_{fsh}$ from $D_{fn}$ for the front detector cells not on the projection lines to yield an image $D_{fPh}$, which is a full two-dimensional image of the subject at the front detector after scatter x-rays have been substantially eliminated.

Alternate embodiments of the method of the present invention operate on the different embodiments of the apparatus described above and in detail below.

By using the apparatus and following the methods described above and in detail below, pair of scatter-free dual-energy images is obtained, from which the material composition data pair for the subject can be readily provided at high accuracy and high spatial resolution.

Thus, an object of the present invention is to provide a method and apparatus for scatter-free dual-energy x-ray imaging using two-dimensional detectors and to provide two scatter-free material composition images of a subject at the spatial resolution as high as a two-dimensional detector array can provide.

A further object of the present invention is to provide an apparatus and method for substantially eliminating the effects of scatter on two-dimensional x-ray detectors.

BRIEF DESCRIPTION OF THE DRAWINGS

For a fuller understanding of the nature and object of the present invention, reference is made to the accompanying drawings, wherein.

DETAILED DESCRIPTION

Introduction

The present invention comprises an apparatus and method for providing scatter-free dual-energy x-ray imaging using two-dimensional detectors and for eliminating scatter from an x-ray image derived from two-dimensional detectors. The basic apparatus includes five components: (1) an x-ray source, (2) a front two-dimensional x-ray detector assembly, (3) a collimator, (4) a rear two-dimensional x-ray detector assembly, and (5) a computer.

Figure 1:
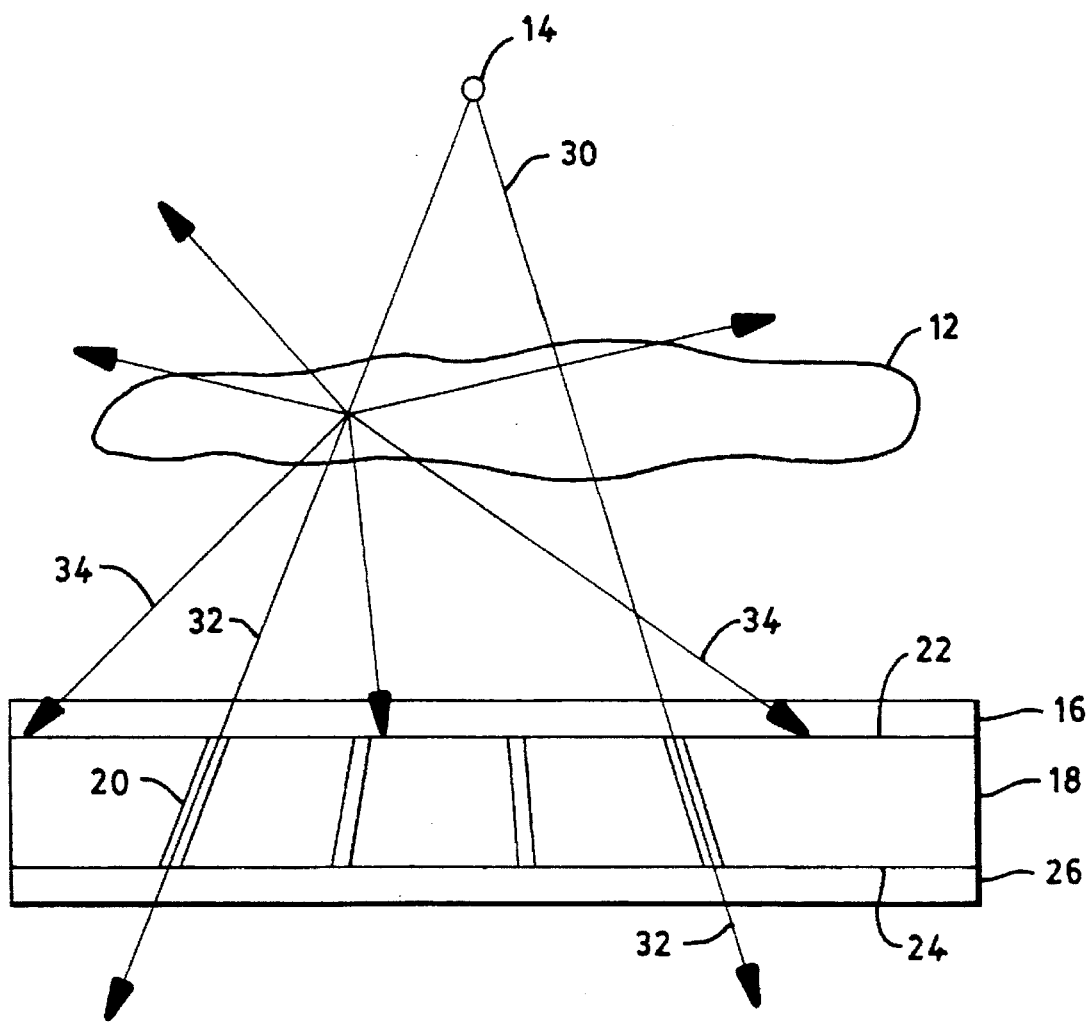
FIG. 1 is a diagram of the basic hardware of the present invention.
Figure 2:
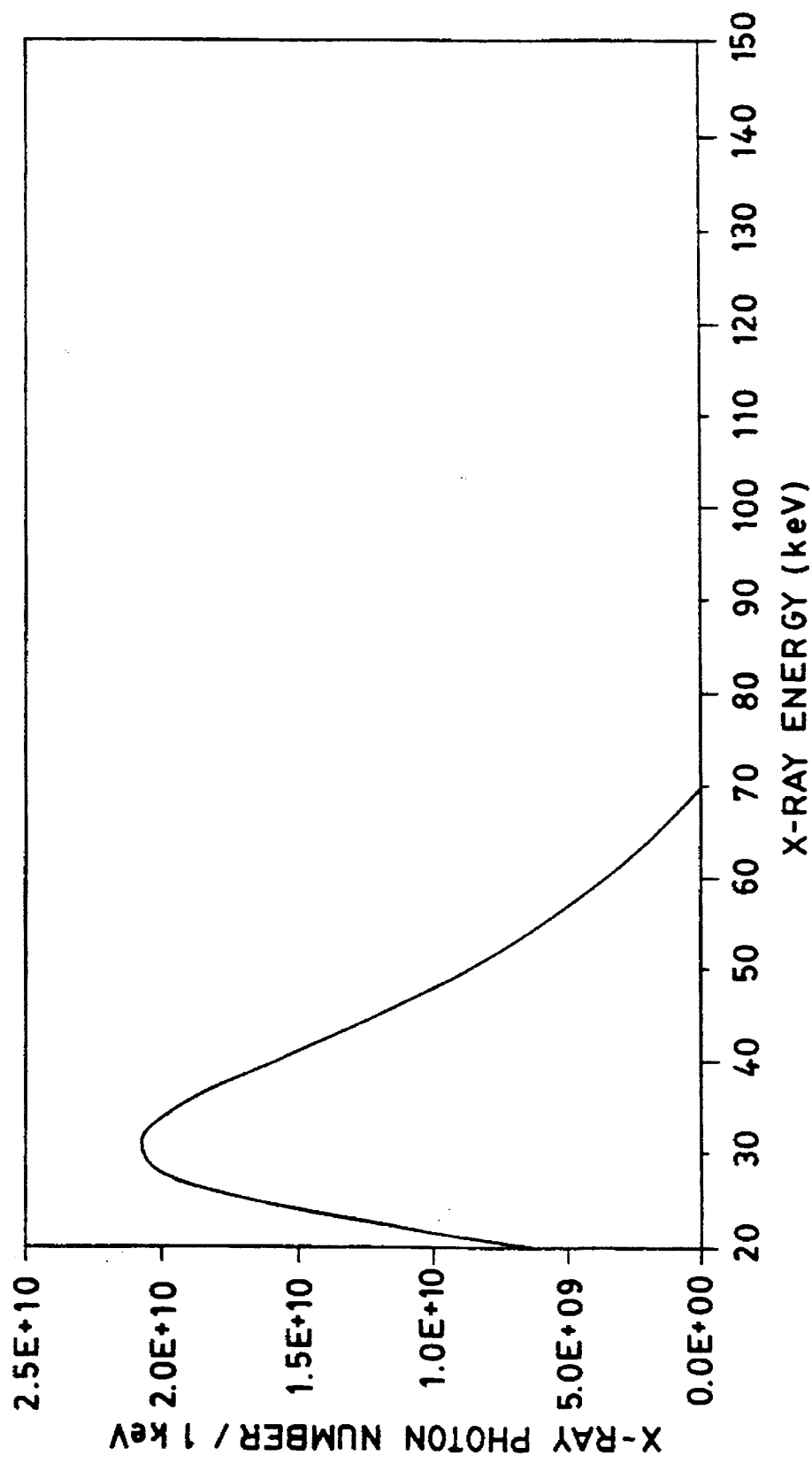
FIG. 2 is a curve describing a typical x-ray source energy spectrum used in the present invention.

As shown in FIG. 1, the subject under examination 12 is located between the x-ray source 14 and the front detector assembly 16. The x-ray source 14 emits x-rays 30, preferably with an energy in the range of from 10 keV to 500 keV, as shown in FIG. 2. The x-ray source 14 is essentially a point source, meaning that the x-rays appear to be emanating from a single point rather than from a larger area. A portion of the x-rays 32 passes through the subject 12 directly to the front detector assembly 16 without a change in their direction of propagation. These x-rays 32 are called the primary x-rays and convey true information about the subject 12. The remainder of the x-rays 34 are randomly scattered as a result of interaction with the material of the subject 12. These x-rays 34 are called scatter and cause a distortion of the true information.

The front detector assembly 16 contains a large number of individual detector cells in a two-dimensional array. Although the present invention is not limited to a particular type of x-ray detector array, there are two basic types. The first uses thin film amorphous silicon as the photodetection medium. The amorphous silicon film has a typical thickness of 1 micrometer (μm) and is sensitive to visible light. The electric charge induced by visible photons is collected by an array of electrodes. An x-ray sensitive scintillation screen is placed in close contact with the entire photosensitive area of the photodetector array. X-rays cause the generation of visible photons in the scintillation screen, which are then detected by the amorphous silicon photodetector array, inducing an electric charge proportional to the x-ray energy absorbed in the screen. This type of x-ray detector array is called an external conversion type x-ray detector. Preferably, the detector array has dimensions of 20 centimeters (cm) by 20 cm or 40 cm by 40 cm for a single detector module. A number of such detector modules can be joined together to provide a larger detector. The cell size for this detector array is in the range of from approximately 50 μm by 50 μm to approximately 1 mm by 1 mm.

A second type of detector array uses an amorphous selenium film or selenium alloy as the x-ray detection medium. The charge induced by x-rays directly in the selenium film is collected by an array of electrodes and is proportional to the energy of the x-rays striking the film. The typical thickness of the selenium film is in the range of from approximately 100 μm to approximately 800 μm. This type of x-ray detector array is called an internal conversion type x-ray detector. A typical amorphous selenium or selenium alloy detector array module has dimensions of 20 cm by 20 cm or 40 cm by 40 cm with a cell size of from approximately 50 μm by 50 μm to approximately 1 mm by 1 mm. A number of such detector modules can be joined together to create a larger detector array.

Other typical two-dimensional detector arrays include charge-couple device (CCD) detectors, thin-film thallium-bromide-based detector arrays, avalanche silicon detector arrays, and phosphor-stimulable computed radiography screens.

The cells of the front detector assembly 16 have variations in their response characteristics. However, these variations are slight and it is assumed that all detector cells have the same response characteristics.

The combination of signals from all of the cells conveys an image of the energy of the x-rays over the area of the front detector assembly 16. Because the cells cannot distinguish between primary x-rays 32 and scatter 34, the front detector assembly 16 conveys an image that is a combination of the primary x-rays 32 and the scatter 34, and is denoted by $$D_f(x,y) = D_{fp}(x,y) + D_{fs}(x,y) \qquad (3)$$

where $D_f$ denotes a front detector assembly 16 image, (x,y) denotes the two-dimensional Cartesian coordinates of a cell of the front detector assembly 16, $D_{fp}(x,y)$ denotes the primary x-ray 32 contribution, and $D_{fs}(x,y)$ denotes the scatter 34 contribution.

The x-ray collimator 18 is a quantity of x-ray-absorbent material having a large number of through holes 20. The holes 20 are fabricated such that their axes are aligned with the direction of propagation of the primary x-rays 32. As a result, the holes 20 permit all x-rays propagating along the axes of the holes 20 to pass through, while all x-rays propagating in directions deviating slightly from the hole axes are nearly completely absorbed by the collimator 18. Thus, only primary x-rays 32 reach the rear detector array 26. The cross-sectional shape of the holes 20 is not important, but for ease in manufacturing, they are preferably round or square. Preferably, the holes 20 are as small as possible, but for cost reasons, they have a diameter that is in the range of from 0.5 mm to 10 mm. If the holes 20 are too large, they will not prevent all of the scatter 34 from reaching the rear detector 26. Preferably, there are as many holes as possible in the collimator 18. The more holes 20 there are in the collimator 18, the greater the accuracy of the measurement at the rear detector 26. However, the collimator material must occupy enough space so that all of the scatter 34 is absorbed. A compromise based on these factors results in a pitch that is preferably between 2 mm and 50 mm. The holes 20 are fabricated such that their axes are aligned with the direction of the travel of the primary x-rays 32, which means that, because the x-rays are emitted from essentially a point source, the holes 20 are not exactly parallel to each other, but are radial to the x-ray source. As the x-ray source 14 is located farther away from the collimator 18, the holes 20 approach being parallel to each other. Preferably, the x-ray source 14 is located between 20 cm and 150 cm from the rear of the collimator 24.

The material of the collimator 18 must ensure that all scatter 34 is absorbed and that none reaches the rear detector 26. The collimator 18 has approximately the same area as the front detector 16 and is preferably between 1 cm and 10 cm in thickness.

After exiting the collimator 18, the x-rays strike the rear detector assembly 26, which works in the same way as the front detector assembly 16. Because of the action of the collimator 18, the image recorded by the rear detector assembly 26 is only that of primary x-rays 32. $D_r$ denotes a rear detector assembly 26 image and (i,j) denotes the two-dimensional Cartesian coordinates of a cell of the rear detector assembly 26. Preferably, the rear detector cells are arranged in a square matrix with from 32 to 8192 cells on a side.

Because the collimator 18 has solid portions that do not allow the passage of some of the primary x-rays 32, a portion of the rear detector cells receive no x-ray energy, resulting in an output of zero for those cells. The rear detector cells that do receive some x-ray energy have a fixed relation with some of the front detector cells. This relation is established by drawing a straight line from the x-ray source 14 through one of the collimator holes 20. This line, called the projection line, intersects a front detector cell and a rear detector cell. The coordinate of the front detector cell on the projection line is denoted as (x(i),y(j)), where (i,j) is the coordinate of the rear detector cell on the same projection line. This relationship is established for all of the collimator holes 20 and stored. The images represented by the composite of the signals from the detector cells of one detector on projections lines only are low-resolution images and are represented by a subscript lower-case 1. The images represented by the composite of the signals from all the detector cells of one detector are high-resolution images and are represented by the subscript lower-case h.

The method of the present invention consists of two parts: a method for dual-energy x-ray data decomposition and a method for eliminating scatter. For the examples and mathematical models used in this application, the subject under examination 12 is assumed to be a human body, where the terms b and s represent the area densities of bone tissue and soft tissue, respectively.

The present invention provides a method of data decomposition based on directly solving dual-energy fundamental equations with continuous x-ray spectra without the need to restrict the thickness of the image subject, and consequently, without the need to conduct corrections for beam hardening effects. The dual-energy x-ray data decomposition method, shown in the flow diagram of FIG. 3, includes: (1) constructing a pair of numerical surface equations $D_H=D_H(b,s)$ and $D_L=D_L(b,s)$ for each detector assembly and saving them for later use, where H and L denote a predetermined high x-ray energy level and low x-ray energy level, respectively; (2) constructing a pair of numerical surface equations $b=b(D_H,D_L)$ and $s=s(D_H,D_L)$ by numerically inverting the equations of step 1 and saving them for later use; (3) determining the desired values for b and s at each discrete cell location by inserting the available data pair $(D_H,D_L)$ into the numerical equations of step 2, or determining the desired values for $D_H,D_L$, or only one of them, at each discrete cell location by inserting the available data pair (b,s) into the numerical equations of step 1.

Figure 4:
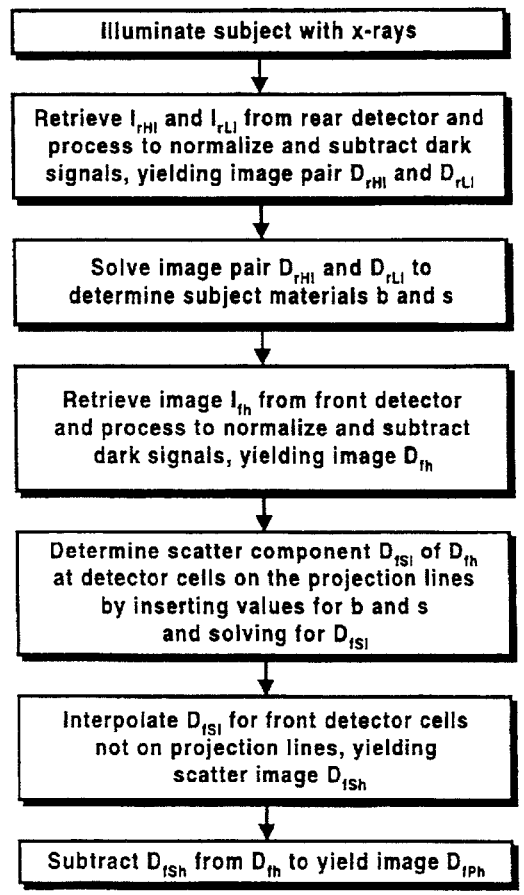
FIG. 4 is a flow diagram of the basic method to eliminate scatter using the hardware of FIG. 1.

The method for eliminating scatter, shown in the flow diagram of FIG. 4, consists of the following steps: (1) illuminating the subject with x-rays from the x-ray source 14; (2) retrieving a low-resolution image pair $I_{rHl}$ and $I_{rLl}$ from the rear detector assembly and processing it to normalize and to subtract dark signals, yielding a low-resolution image pair $D_{rHl}$ and $D_{rLl}$ that are functions of the subject materials; (3) solving the image pair $D_{rHl}$ and $D_{rLl}$ to determine the subject materials b and s; (4) retrieving a high-resolution image $I_{fh}$ from the front detector and processing it to normalize and to subtract dark signals, yielding a high-resolution image $D_{fh}$, which is the sum of primary x-rays and scatter x-rays; (5) determining the low-resolution scatter component $D_{fsl}$ of image $D_{fh}$ at detector cells on the projection lines by inserting the values for b and s and solving for $D_{fsl}$; (6) interpolating $D_{fsl}$ for those front detector cells not on the projection lines, yielding the high-resolution scatter image $D_{fsh}$; and (7) subtracting the image $D_{fsh}$ from $D_{fh}$ to yield an image $D_{fph}$, which is a full two-dimensional image of the subject at the front detector after scatter x-rays have been substantially eliminated.

The first step consists of illuminating the subject with high-energy x-rays and low-energy x-rays. There are two approaches to accomplishing this. The first is to use two x-ray pulses of different energy levels. For this approach, only one detector array is necessary in the rear detector assembly 26 because the two energy levels are temporally separated. The second approach is to use a pulse or a continuous x-ray emission that spans a spectrum of energies. For this approach, two detector arrays are needed in the rear detector assembly 26, where one detector detects the high-energy x-rays and the other detects the low-energy x-rays.

The second step consists of retrieving a pair of low-resolution images $I_{rHl}(i,j)$, $I_{rLl}(i,j)$ from the rear detector 26. The image $I_{rHl}(i,j)$ results from illuminating the subject with the high-energy x-rays or from the high-energy detector and the image $I_{rLl}(i,j)$ results from illuminating the subject with the low-energy x-rays or from the low-energy detector The image pair $I_{rHl}(i,j)$, $I_{rLl}(i,j)$ is processed by computer software to normalized the data and to subtract dark signals. Both of these procedures must be used by any x-ray imaging technology and are well known in the art. Throughout this specification, all images retrieved from the detectors 16, 26 are assumed to have been processed to normalized the data and to subtract dark signals following retrieval. This image pair $D_{rHl}$, $D_{rLl}$ constitutes a dual-energy x-ray image pair.

The third step consists of determining the subject material compositions b and s from the image data pair $D_{rH}(i,j)$ and $D_{rL}(i,j)$. For each pair of dual-energy x-ray data $(D_{rH},D_{rL})$ at the point (i,j), a pair of material composition data (b,s) along the projection line can be determined from the data base provided by the data decomposition method, as explained below.

The fourth step consists of retrieving the high-resolution image $I_{fh}(x,y)$ from the front detector 16 and processing it to normalized the data and to subtract dark signals, yielding the high-resolution image $D_{fh}(x,y)$.

The fifth step consists of calculating the low-resolution scatter component of the image $D_{fh}$ at the front detector cells on the projections lines (x(i),y(j)). By using the data base, $D_H(b,s)$ and $D_L(b,s)$ provided by the data decomposition method for the front detector assembly 16, the signal pair $D_H$, $D_L$ is determined from the subject material compositions b and s found in step 3. If the front detector assembly 16 has only one detector array, the corresponding signal is $D_f(b,s)$ as measured or calculated for the system in advance. Then the primary x-ray signal on the front detector $D_{fPl}(x(i),y(j))=D(b(i,j),s(i,j))$.

As explained above, the images from the rear detector assembly 26 are free of scatter. So, the scatter image from the front detector assembly 16 can be found from the equation $$D_{fSl}(x(i),(j))=D_{fh}(x(i),y(j))-D_{fPl}(x(i),y(j)) \qquad (4)$$

which yields the scatter image at the front detector cells on the projection lines, or the low-resolution scatter image.

The sixth step consists of interpolating the values for the low-resolution scatter image $D_{fSl}(x(i),y(j))$ to include those detector cells that are not on projection lines, yielding the high-resolution scatter image $D_{fSh}(x,y)$. The interpolation does not cause loss of accuracy because of the nature of the physical scattering process. The scatter 34 is essentially caused by Compton scattering, which has a substantially uniform angular distribution in the preferred x-ray energy range. Both empirical data and theoretical calculations show that scatter always has a substantially smooth distribution on a two-dimensional image plane. This means that the change in scatter intensity between adjacent cells is small and smooth. Thus, the error incurred by increasing the number of detector cell data points is negligible in comparison with other error sources, such as statistical fluctuations of x-ray photon numbers and instrument measurement error.

The final step consists of subtracting the high-resolution scatter image $D_{fSh}(x,y)$ from $D_{fh}(x,y)$ using the following equation derived from equation (3):

$$D_{fPh}(x,y)=D_{fh}(x,y)-D_{fSh}(x,y) \qquad (5)$$

Equation (5) yields an image $D_{fPh}(x,y)$ corresponding to an image that would result if only primary x-rays 32 impinged on the front detector 16.

Because the image data acquired from the detectors is highly accurate, the data decomposition method of the present invention is highly accurate, and the mathematical calculations are performed with great precision, the final result is a highly accurate image of the subject comprised solely of primary x-rays.

First Embodiment

Figure 5:
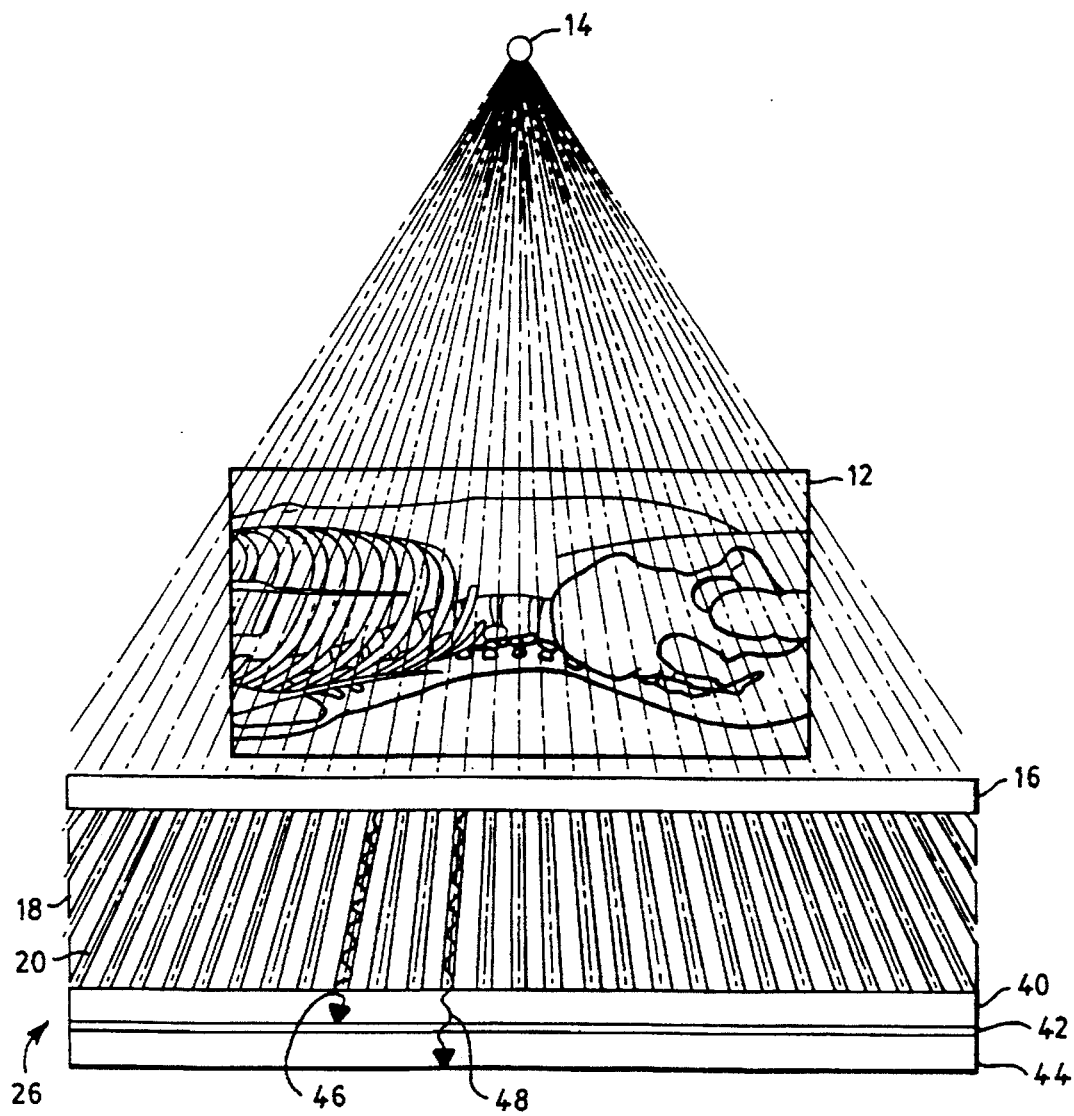
FIG. 5 is a diagram of the first embodiment of the present invention.

In the first embodiment of the apparatus, shown in FIG. 5, the rear detector assembly 26 is constructed as a dual-energy x-ray imaging detector. It has a low-energy two-dimensional detector 40, an x-ray energy spectral filter 42, and a high-energy two-dimensional detector 44. The filter 42 operates in the conventional manner. It has a transmission function of $\exp(-\mu(E) \times d)$, where E is the energy of the x-rays, $\mu(E)$ is the mass absorption coefficient of the filter material, and d is the thickness of the filter 42. Because the absorption of x-rays is dependent upon the energy of the x-rays (the mass absorption coefficient is a function of E), the filter 42 absorbs more of the low-energy x-rays 46 than high-energy x-rays 48. Thus, the proportion of high-energy x-rays 48 to low-energy x-rays 46 after the filter 42 is larger than before the filter 42 and the average normalized x-ray energy after the filter 42 is larger than before the filter 42. The image detected by the low-energy detector 40 is denoted by $D_{rL}(i,j)$ and the image detected by the high-energy detector 44 is denoted by $D_{rH}(i,j)$. Preferably, the low-energy x-rays have an energy of from 10 keV to 100 keV and high-energy x-rays have an energy of from 30 keV to 500 keV, with the high-energy x-rays having a higher energy than the low-energy x-rays.

The reason it is necessary to use a pair of images $D_{rH}(i,j)$ and $D_{rL}(i,j)$ on the (i,j) plane to find the scatter image is that only a pair of dual-energy images can uniquely determine two unknown material compositions, in this case b(i,j) and s(i,j), which vary from subject to subject. In short, there are two independent variables, b(i,j) and s(i,j). Standard mathematics states that in order to find the solution to two independent variables, two independent simultaneous equations are needed. The two independent simultaneous equations are formed by using two different x-ray energies. If only one image on the (i,j) plane is used, the result will be dependent upon prior knowledge of the subject 12, which is highly undesirable.

Figure 6:
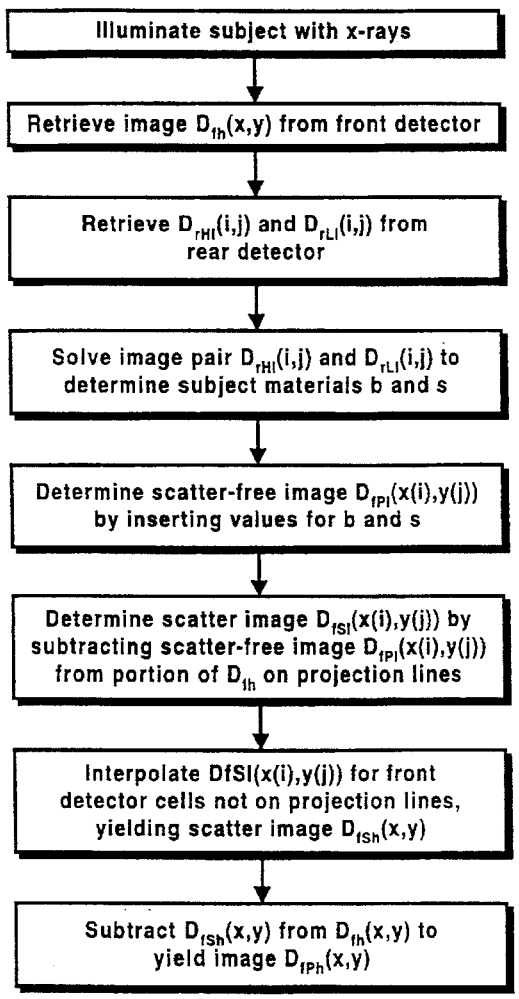
FIG. 6 is a flow diagram of the method of the first embodiment using the hardware of FIG. 5.

A flow diagram describing the method for determining a scatter-free image using the hardware of the first embodiment is shown in FIG. 6. The x-ray source 14 emits x-rays with a uniform spatial distribution and with an energy spectrum of $\Phi_0(E)$. The x-rays passing through the subject 12 carry information on the thickness of the subject 12 expressed as mass area density in units of grams/centimeter$^2$ (g/cm$^2$). The image induced by the x-rays incident on the front detector 16 is denoted as $D_{fh}(x,y)$ and is $$D_{fh}(x,y) = \int [\Phi_0(E) \times \exp(-(\mu_b(E) \times b(x,y) + \mu_s(E) \times s(x,y))] \times S_f(E)dE + \int \Phi_S(E) \times S_f(E)dE \qquad (6)$$

where $\mu_b(E)$ is the mass absorption coefficient of bone tissue and $\mu_s(E)$ is the mass absorption coefficient of soft tissue, both expressed in units of centimeters$^2$/gram (cm$^2$/g). Both of these values are known, having been determined experimentally and tabulated many years ago. The term $[\Phi_0(E) \times \exp(-(\mu_b(E) \times b(x,y) + \mu_s(E) \times s(x,y))]$ is the energy spectrum of the primary x-rays incident on the front detector 16 after passing through the subject 12, where exp() denotes the value e raised to the power specified in the parenthesis. $S_f(E)$ is the x-ray spectral sensitivity (the electrical signal from the detector as a function of x-rays with energy E incident upon the detector) of the front detector 16. Note that $S_f(E)$ includes the x-ray transmission factor that accounts for the absorption of x-rays between the subject 12 and the front detector 16. Such absorption is due, for example, to the front detector protective case material. The term $\int \Phi_s(E) \times S_f(E) dE$ represents the signal caused by scatter. Each pair of coordinates (x,y) corresponds to a front detector cell.

The rear detector assembly 26 has two detectors 40, 44, so there are two low-resolution images $D_{rL}(i,j)$ and $D_{rH}(i,j)$, which are $$D_{rL}(i,j) = \int [\Phi_0(E) \times \exp(-(\mu_b(E) \times b(i,j) + \mu_s(E) \times s(i,j)))] \times S_{rL}(E) dE \quad (7a)$$

and $$D_{rH}(i,j) = \int [\Phi_0(E) \times \exp(-(\mu_b(E) \times b(i,j) + \mu_s(E) \times s(i,j)))] \times S_{rH}(E) dE \quad (7b)$$

Note that, as above, $S_{rL}(E)$ and $S_{rH}(E)$ include the x-ray transmission factor that accounts for the absorption of x-rays between the subject 12 and the respective rear detectors 40, 44. Such absorption is due, for example, to the front detector assembly 16, the spectral filter 42, and the rear detector protective case.

Equations (7a) and (7b) constitute a simultaneous equation pair, where the values for the signal pair $D_{rL}(i,j)$, $D_{rH}(i,j)$ are known quantities, being evaluated from the electrical signals of the rear detectors 40, 44. The energy dependent functions $\Phi_0(E) \times S_{rL}(E)$ and $\Phi_0(E) \times S_{rH}(E)$ are not directly known but can be determined through experimental measurements and calculations. The data decomposition method described below provides a way to determine these quantities in advance of image operations. b(i,j) and s(i,j) are the unknown quantities for which equation pair (5a,5b) must be solved, as described below. Generally speaking, in mathematics, such a nonlinear simultaneous equation pair is too complicated to be solvable because it may have an infinite number of solutions, may have multiple-value solutions, or may not have any solution. However, for the specific case of x-ray imaging, where the energy range is limited, preferably between 10 and 500 keV, as described above, a unique solution always exists.

Now that the values for b(i,j) and s(i,j) are known, the front low-resolution scatter-free image $D_{fPl}(x,y)$ can be obtained for those front detector cells (x(i),y(j)) that are on the projection lines. $D_{fPl}(x(i),y(j))$ is the signal induced by primary x-rays only at the detector cell (x(i),y(j)) on the front detector, and is $$D_{fPl}(x(i),y(j)) = \int [\Phi_0(E) \times \exp(-(\mu_b(E) \times b(i,j) + \mu_s(E) \times s(i,j))] \times S_f(E) dE \quad (8)$$

where (x(i),y(j)) is the coordinate of the front detector cell (x,y) lying on the same projection line as the rear detector cell (i,j).

Next, the low-resolution front scatter image $D_{fSl}(x(i),y(j))$ is determined by applying equation (4). Because of the physical nature of scatter, as described above, the low-resolution scatter image $D_{fSl}(x(i),y(j))$ can be extended to the entire (x,y) plane through interpolation without losing accuracy, yielding the high-resolution scatter image $D_{fSh}(x,y)$. The high-resolution scatter image $D_{fSh}(x,y)$ is subtracted from the image $D_{fh}(x,y)$, yielding the high-resolution scatter-free signal $D_{fPh}(x,y)$.

It is now clearer why it is necessary to acquire a pair of dual-energy x-ray images $D_{rL}(i,j)$, $D_{rH}(i,j)$ to determine the scatter. The two material composition images b(i,j) and s(i,j) can only be uniquely determined from a pair of dual-energy images $D_{rL}(i,j)$, $D_{rH}(i,j)$. To put it another way, because the x-rays have a continuous spectrum, no constant ratio exists between the signals measured by the front detector and the signals measured by the rear detector. If only one image at the rear detector is used, it would be found that the signal ratio between the front detector and the rear detector is dependent on the energy spectrum $[\Phi_0(E) \times \exp(-(\mu_b(E) \times b(i,j) + \mu_s(E) \times s(i,j))]$, or dependent on the image subject. Consequently, the scatter image on the front detector could not be determined.

However, in the special case where the x-rays can be approximated as having only a single energy or an average energy $E_0$, it is possible to use only one rear detector image to remove the scatter from the front detector image. In this special case, there exists a constant ratio C between the signal of the rear detector $D_{rP}(i,j)$ and the signal of the front detector $D_{fP}(x(i),y(j))$ for the detector cells lying on the same projection line. The following relationships show this to be true:

$$D_{fPi}(x(i),y(j)) = \Phi_0(E_0) \times \quad (9)$$
$$\exp(-(\mu_b(E_0) \times b(x(i),y(j)) + \mu_s(E_0) \times s(x(i),y(j)))) \times S_f(E_0)$$

and $$D_{rl}(i,j) = \Phi_0(E_0) \times \exp(-(\mu_b(E_0) \times b(i,j) + \mu_s(E_0) \times s(i,j)) \times S_r(E_0) \quad (10)$$

yielding $$\frac{D_{fPi}(x(i),y(j))}{D_{rl}(i,j)} = \frac{S_f(E_0)}{S_r(E_0)} = C \quad (11)$$

The constant C is independent of image subject and can be measured before using the system for imaging operations. Using the constant C, $D_{fPi}(x(i),y(j))$ is calculated from $D_{rl}(i,j)$, then $D_{fPh}(x,y)$ is determined by applying equation (4) to get $D_{fSi}(x(i),y(j))$, extending it to $D_{fSh}(x,y)$, and finally applying equation (5).

Second Embodiment

Figure 7:
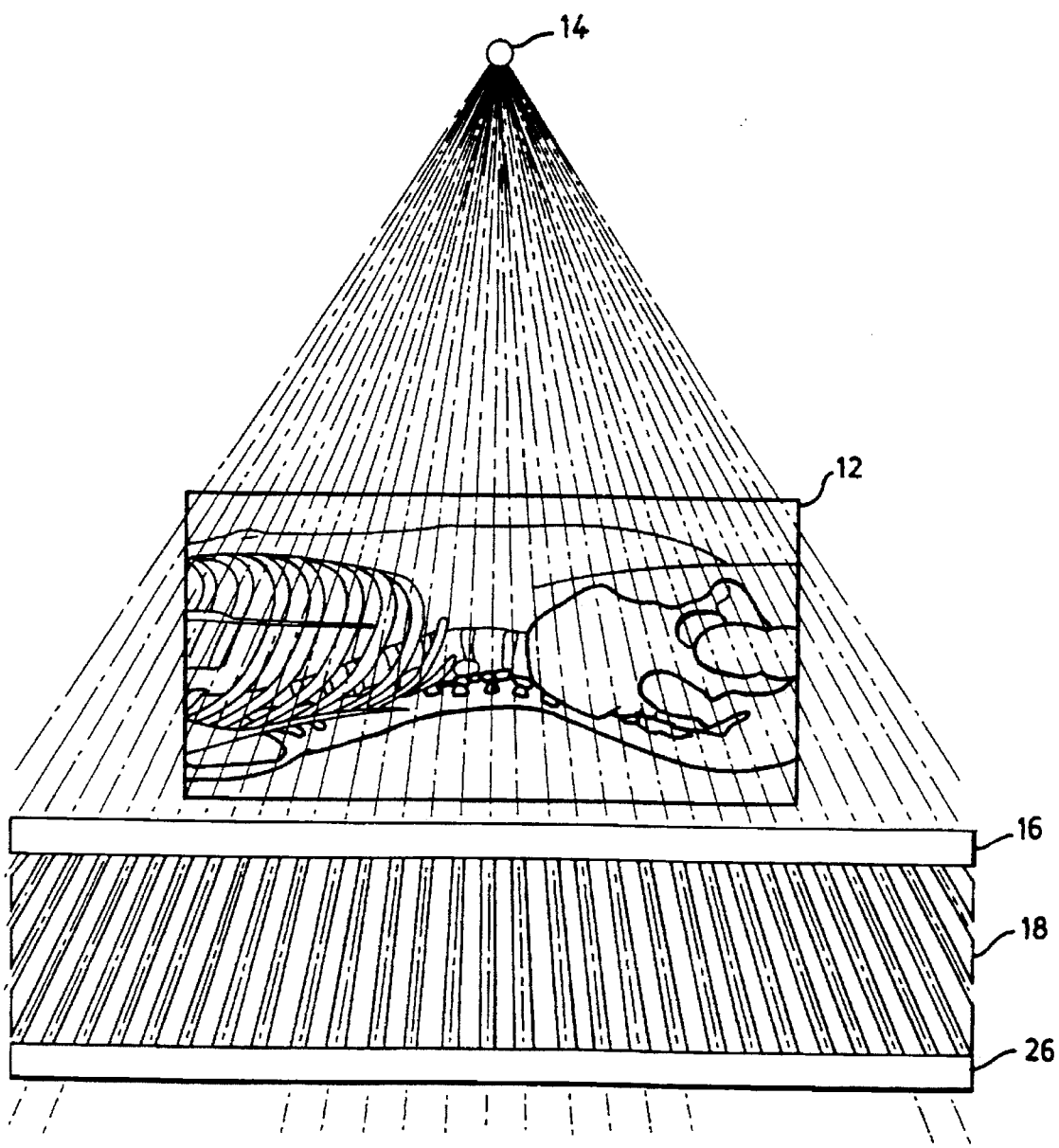
FIG. 7 is a diagram of the second embodiment of the present invention.

In this embodiment, shown in FIG. 7, each detector assembly 16, 26 has only one detector. The x-ray source 14 emits two consecutive pulses, a low-energy pulse followed by a high-energy pulse. In an alternate configuration, the high-energy pulse is emitted first. Preferably, in both configurations, the low-energy pulse is approximately from 10 keV to 100 keV and the high-energy pulse is approximately from 30 keV to 500 keV, with the high-energy pulse always higher in energy than the low-energy pulse.

Figure 8:
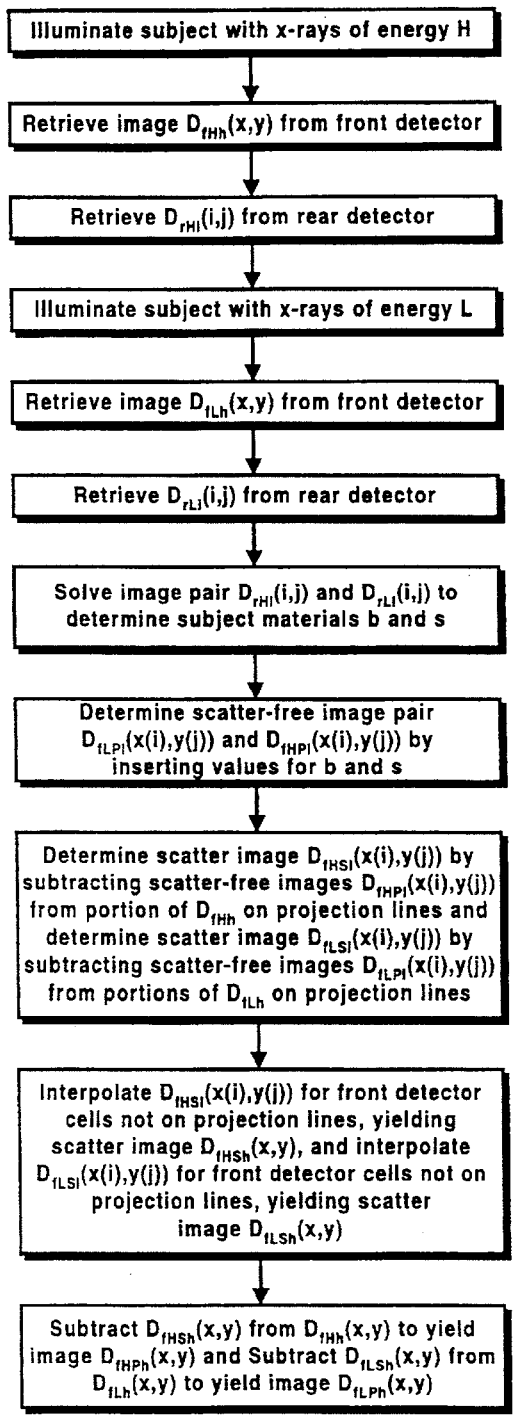
FIG. 8 is a flow diagram of the method of the second embodiment using the hardware of FIG. 7.

As described with respect to the first embodiment above, the low-resolution scatter-free image pair $D_{rL}(i,j)$, $D_{rH}(i,j)$ from the rear detector is used to first determine the low-resolution scatter image pair on the front detector 16. In this embodiment, a pair of low-resolution scatter images $D_{fHSl}(x(i),x(j))$, $D_{fLSl}(x(i),x(j))$ is obtained for the front detector 16 operated at high energy and at low energy, respectively. After interpolation of the resulting scatter image pair to a high-resolution image pair $D_{fHSh}(x,y)$, $D_{fLSh}(x,y)$ to cover all (x,y) cells and subtracting the high-resolution scatter image pair from the composite image pair $D_{fLh}(x,y)$, $D_{fHh}(x,y)$, a pair of high-resolution scatter-free images $D_{fLPh}(x,y)$, $D_{fHPh}(x,y)$ are obtained. The method is detailed as follows:

As shown in FIG. 8, the high-resolution image $D_{fHh}(x,y)$ is retrieved from the front detector 16 and low-resolution image $D_{rHh}(i,j)$ is retrieved from the rear detector 26 following the high-energy pulse. The high-resolution image $D_{fLh}(x,y)$ is retrieved from the front detector 16 and the low-resolution image $D_{rLh}(i,j)$ is retrieved from the rear detector 26 following the low-energy pulse. From these two consecutive operations of data acquisition, two pairs of images are obtained. The first pair includes the high-resolution images from the front detector 16 and are $$D_{fHh}(x,y) = \int [\Phi_{0H}(E) \times \exp(-(\mu_b(E) \times b(x,y) + \mu_s(E) \times s(x,y))] \times S_f(E) dE + \int \Phi_{fS}(E,x,y) \times S_f(E) dE \quad (12a)$$

and $$D_{fLh}(x,y) = \int [\Phi_{0L}(E) \times \exp(-(\mu_b(E) \times b(x,y) + \mu_s(E) \times s(x,y))] \times S_f(E) dE + \int \Phi_{fS}(E,x,y) \times S_f(E) dE \quad (12b)$$

and the second pair includes the low-resolution images from the rear detector 26 and are $$D_{rHh}(i,j) = \int [\Phi_{0H}(E) \times \exp(-(\mu_b(E) \times b(i,j) + \mu_s(E) \times s(i,j))] \times S_r(E) dE \quad (13a)$$

and $$D_{rLh}(i,j) = \int [\Phi_{0L}(E) \times \exp(-(\mu_b(E) \times b(i,j) + \mu_s(E) \times s(i,j))] \times S_r(E) dE \quad (13b)$$

In the equation pair (13a,13b), the acquired low-resolution image data are free of scatter radiation. By using the methods described below, the simultaneous equation pair (13a,13b) is solved to find the solutions for the pair of material composition images $b(i,j)$ and $s(i,j)$.

As described above with reference to the first embodiment, because each rear detector cell position in the (i,j) plane corresponds to a known front detector cell position $(x(i),y(j))$ in the $(x,y)$ plane and because the rear detector cell $(i,j)$ and front detector cell $(x(i),y(j))$ lie on the same projection line, the low-resolution front detector primary image pair $D_{fHPl}(x(i),y(j))$, $D_{fLPl}(x(i),y(j))$ are determined from the rear detector primary image pair $D_{rHl}(i,j)$, $D_{rLl}(i,j)$. The front detector scatter image pair $D_{fHSl}(x(i),y(j))$, $D_{fLSl}(x(i),y(j))$ are found by the equations $$D_{fHSl}(x(i),y(j)) = D_{fHl}(x(i),y(j)) - D_{fHPl}(x(i),y(j)) \quad (14a)$$

and $$D_{fLSl}(x(i),y(j)) = D_{fLl}(x(i),y(j)) - D_{fLPl}(x(i),y(j)) \quad (14b)$$

As above, the low-resolution scatter images are extended to the front detector cells not on projection lines through interpolation without loss of accuracy to yield the high-resolution scatter image pair $D_{fHSh}(x,y)$, $D_{fLSh}(x,y)$. The high-resolution scatter-free images on the front detector assembly are denoted as $D_{fHPh}(x,y)$ and $D_{fLPh}(x,y)$ and are $$D_{fHPh}(x,y) = D_{fHh}(x,y) - D_{fHSh}(x,y) \quad (15a)$$

and $$D_{fLPh}(x,y) = D_{fLh}(x,y) - D_{fLSh}(x,y) \quad (15b)$$

The image pair $D_{fHPh}(x,y)$, $D_{fLPh}(x,y)$ is a pair of dual-energy x-ray images without scatter. This image pair in turn relates to the material composition of the subject by the equations $$D_{fHPh}(x,y) = \int [\Phi_{0H}(E) \times \exp(-(\mu_b(E) \times b(x,y) + \mu_s(E) \times s(x,y))] \times S_f(E) dE \quad (16a)$$

and $$D_{fLPh}(x,y) = \int [\Phi_{0L}(E) \times \exp(-(\mu_b(E) \times b(x,y) + \mu_s(E) \times s(x,y))] \times S_f(E) dE \quad (16b)$$

Thus, in addition to providing one scatter-free image, this embodiment provides a pair of scatter-free dual-energy images in the equation pair (16a,16b). This equation pair is the fundamental dual-energy x-ray imaging equations with the unprecedented feature that scatter radiation has been substantially removed. In the equation pair (16a,16b), the values $D_{fLPh}(x,y)$ and $D_{fHPh}(x,y)$ are known from the above-described calculations conducted on the image pair $D_{fHh}(x,y)$, $D_{fLh}(x,y)$ obtained from the front detectors 16, and on the image pair $D_{rLl}(i,j)$, $D_{rHl}(i,j)$ obtained from the rear detector 26. The unknown values are the two material composition images $b(x,y)$ and $s(x,y)$.

The dual-energy x-ray data decomposition method can be applied to the equation pair (16a,16b). As a result, by using the quantitative relationships $b=b(D_H,D_L)$ and $s=s(D_H,D_L)$ provided by the data decomposition method, a pair of high-resolution images $b(x,y)$ and $s(x,y)$ are readily obtained point by point for all front detector cells $(x,y)$. The solution of the two-component material composition images $b(x,y)$ and $s(x,y)$ has a spatial resolution as high as the front detector 16 can provide.

From a technology point of view, the first embodiment and second embodiment use essentially the same elements and essentially the same methods. However, from an application point of view, dual-energy x-ray imaging using two-dimensional detectors without scatter is an independent and very important area. The goal of dual-energy x-ray imaging is to find two material composition images of the subject at the spatial resolution as high as the two-dimensional detectors can provide. This invention not only provides a method and apparatus for removing scattering from two-dimensional detectors, but at the same time also provides a method and apparatus for dual-energy x-ray imaging using two-dimensional detectors.

The interrelationship between the method for removing scatter radiation in two-dimensional detectors and the method for dual-energy x-ray imaging using two-dimensional detectors can be summarized as follows:

1. The method for removing scatter radiation from two-dimensional detectors utilizes and hinges on the method of dual-energy x-ray imaging free of scatter. Without dual-energy x-ray imaging, the scatter radiation cannot be accurately removed.

2. The method for dual-energy x-ray imaging using two-dimensional detectors utilizes and hinges on the method of removing scatter radiation. Without substantially removing scatter from two-dimensional detectors, the accuracy of dual-energy x-ray imaging would be so degraded as to be meaningless.

This invention solves these two problems in a unified system. The methods of the prior art fail to solve either of the two problems. The most important reason may be attributed to the failure of prior art methods to recognize the interdependency of the removal of scatter and the use of dual-energy imaging.

An alternate to the second embodiment substitutes an x-ray source having a switching high-voltage power supply. The switching high-voltage x-ray source generates x-rays continuously, alternating between high-energy x-rays and low-energy x-rays. The switching high-voltage x-ray source can be treated as a repetitive double-pulse x-ray source.

Another alternate to the second embodiment inserts an x-ray energy filter between the x-ray source and the subject at the moment the x-ray source switches to generate the high-energy x-rays. The synchronization between the insertion of the filter and the switching high-voltage or double-pulse is preferably implemented by using a motor drive. The filter absorbs more of the low-energy x-rays, resulting in an increase in the energy difference between the low-energy x-rays and the high-energy x-rays.

Third Embodiment

Figure 9:
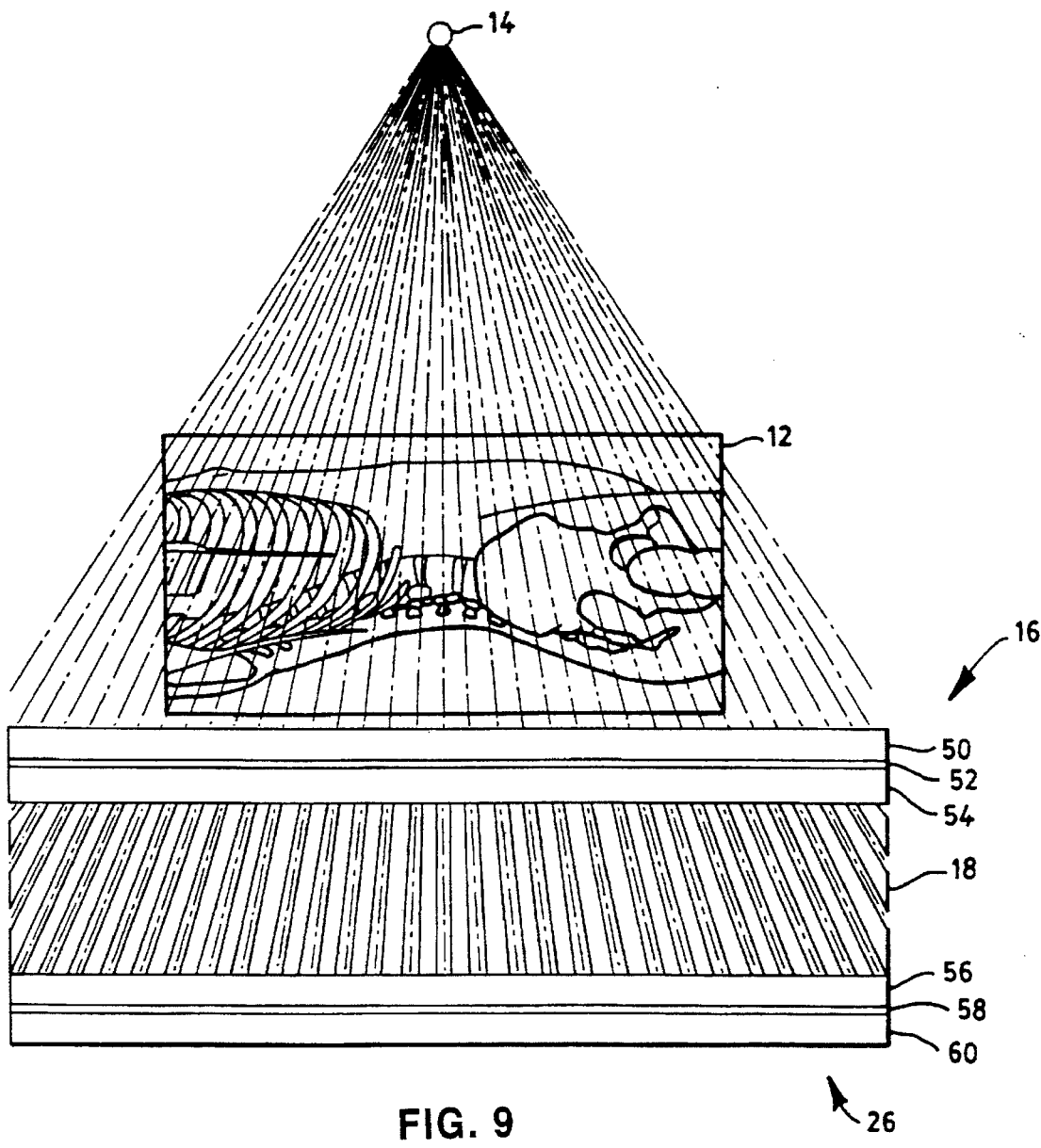
FIG. 9 is a diagram of the third embodiment of the present invention.

The third embodiment, shown in FIG. 9, is also a method for dual-energy x-ray imaging using a pair of two-dimensional detector assemblies. The x-ray source 14 is a constant potential x-ray source that emits steady state x-rays, single pulse x-rays, or repetitive pulse x-rays with the same energy spectrum. The front detector assembly 16 has a low-energy two-dimensional detector 50, an x-ray energy spectral filter 52, and a high-energy two-dimensional detector 54. The rear detector assembly 26 also has a low-energy two-dimensional detector 56, an x-ray energy spectral filter 58, and a high-energy two-dimensional detector 60. The filters 52, 58 operate in the conventional manner as described above with reference to the first embodiment. The front high-energy detector 54 is sensitive to higher x-ray energies than the front low-energy detector 50 and the rear high-energy detector 60 is sensitive to higher x-ray energies than the rear low-energy detector 56. But, in addition, the rear low-energy detector 56 is sensitive to higher x-ray energies than the front high-energy detector 54. This is due to the fact that, by the time the x-rays reach the rear detector 26, they have already passed through the both front detectors 50, 54 and the front spectral filter 52, causing the lower-energy x-rays to have been filtered out.

Figure 10:
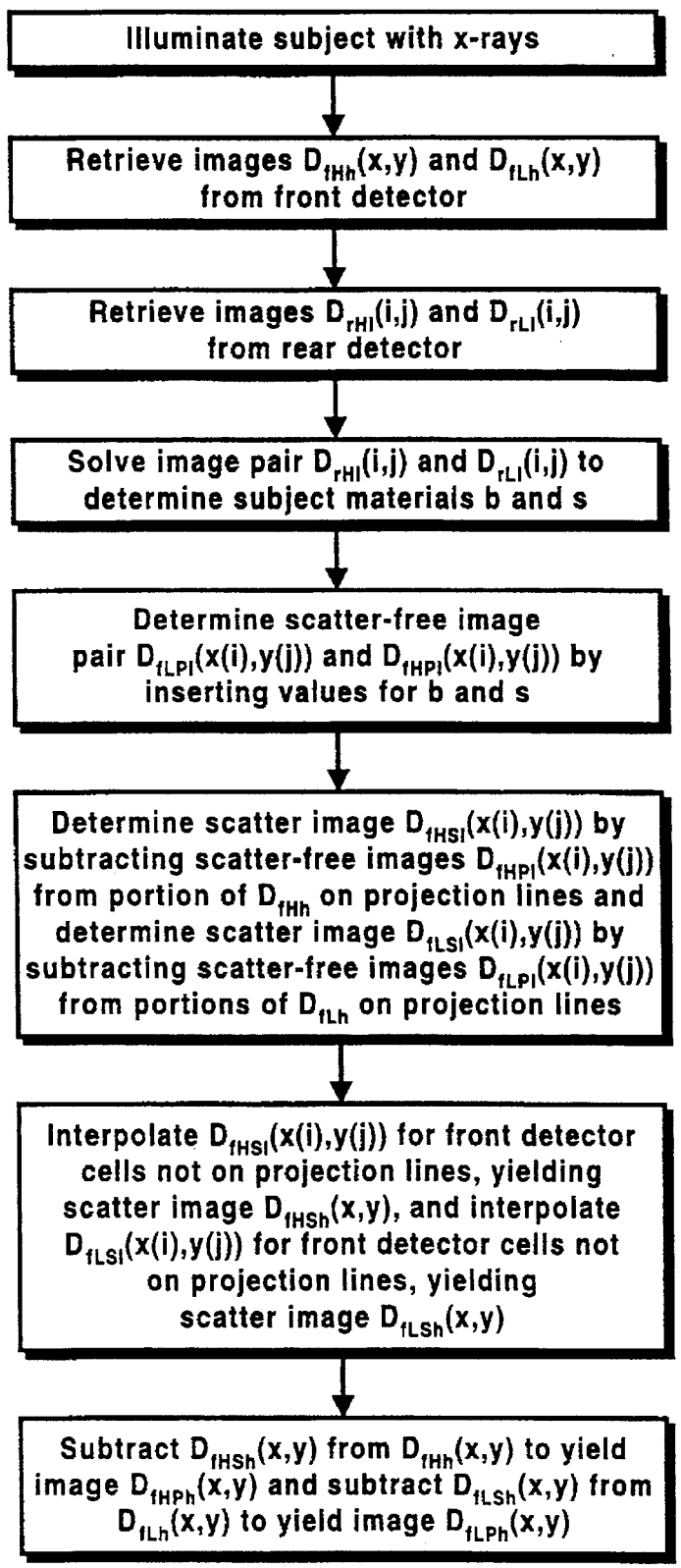
FIG. 10 is a flow diagram of the method of the third embodiment using the hardware of FIG. 9.
Figure 11A:
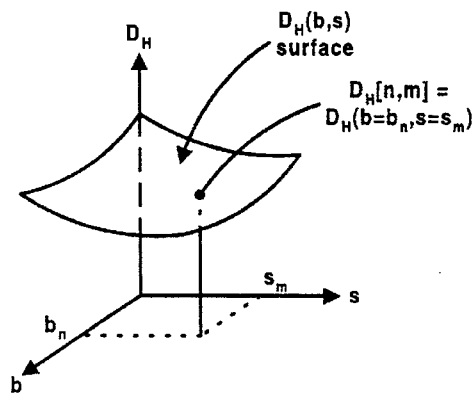
FIG. 11a to 11d is a graphically representation of a method for inverting a data table.
Figure 11B:
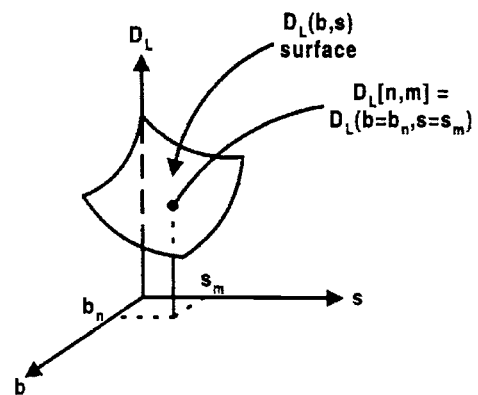
Figure 11C:
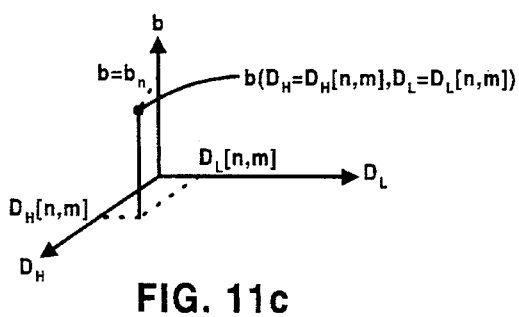
Figure 11D:
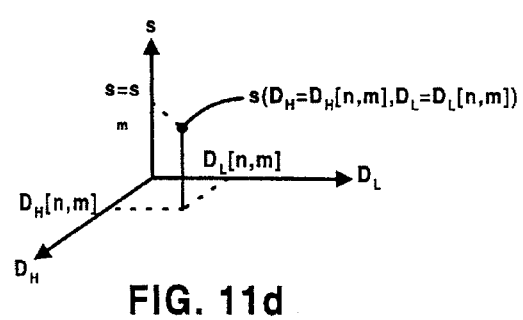

This embodiment requires only single-pulse, constant-energy x-rays, as in the first embodiment, rather than the dual-energy x-ray source of the second embodiment. As shown in FIG. 10, following a single-pulse x-ray, two pairs of dual-energy x-ray images are acquired. The first pair includes the high-resolution images $D_{fLh}(x,y)$ from the low-energy front detector 50 and $D_{fHh}(x,y)$ from the high-energy front detector 54, and are $$D_{fHh}(x,y) = \int [\Phi_0(E) \times \exp(-(\mu_b(E) \times b(x,y) + \mu_s(E) \times s(x,y)))] \times S_{fH}(E)dE + \int \Phi_{fS}(E,x,y) \times S_{fH}(E)dE \quad (17a)$$

and $$D_{fLh}(x,y) = \int [\Phi_0(E) \times \exp(-(\mu_b(E) \times b(x,y) + \mu_s(E) \times s(x,y)))] \times S_{fL}(E)dE + \int \Phi_{fS}(E,x,y) \times S_{fL}(E)dE \quad (17b)$$

and the second pair includes the low-resolution images $D_{rLl}(i,j)$ from the low-energy rear detector 56 and $D_{rHl}(i,j)$ from the high-energy rear detector 60, and are $$D_{rHl}(i,j) = \int [\Phi_0(E) \times \exp(-(\mu_b(E) \times b(i,j) + \mu_s(E) \times s(i,j)))] \times S_{rH}(E)dE \quad (18a)$$

and $$D_{rLl}(i,j) = \int [\Phi_0(E) \times \exp(-(\mu_b(E) \times b(i,j) + \mu_s(E) \times s(i,j)))] \times S_{rL}(E)dE \quad (18b)$$

Note that, because a single-energy x-ray source is used, the x-ray energy spectrum $\phi_0(E)$ is the same for all of the images. Note also that $S_{fH}(E)$, $S_{fL}(E)$, $S_{rH}(E)$, and $S_{rL}(E)$ include not only the energy spectral sensitivity of the corresponding detector but also include all transmission factors that account for x-ray absorption between the subject and the respective detector.

As described above with relation to the second embodiment, the simultaneous equation pair (18a,18b) does not contain scatter and holds true for each point in the rear image plane (i,j). Thus, equation pair (18a,18b) can be solved to yield a pair of material composition images b(i,j), s(i,j) for each cell in the (i,j) plane. This image pair is used to determine the low-resolution scatter image pair $D_{fHSl}(x(i),y(j))$, $D_{fLSl}(x(i),y(j))$ in the same way as for the equation pair (14a,14b). Scatter image pair $D_{fHSl}(x(i),y(j))$, $D_{fLSl}(x(i),y(j))$ are then used to determine the high-resolution scatter image pair $D_{fHSh}(x,y)$, $D_{fLSh}(x,y)$, as described above in the second embodiment. By subtracting the calculated high-resolution scatter image pair $D_{fHSh}(x,y)$, $D_{fLSh}(x,y)$ from the front detector 16 high-resolution image pair $D_{fHh}(x,y)$, $D_{fLh}(x,y)$, the fundamental dual-energy equations free of scatter $D_{fHPh}(x,y)$ and $D_{fLPh}(x,y)$ are obtained and are $$D_{fLPh}(x,y) = \int [\Phi_0(E) \times \exp(-(\mu_b(E) \times b(x,y) + \mu_s(E) \times s(x,y)))] \times S_{fL}(E)dE \quad (19b)$$

and $$D_{fHPh}(x,y) = \int [\Phi_0(E) \times \exp(-(\mu_b(E) \times b(x,y) + \mu_s(E) \times s(x,y)))] \times S_{fH}(E)dE \quad (19a)$$

Using the inversion method described below, a pair of high accuracy high-resolution material composition images b(x,y) and s(x,y) are obtained.

Data Decomposition Method

Figure 3:
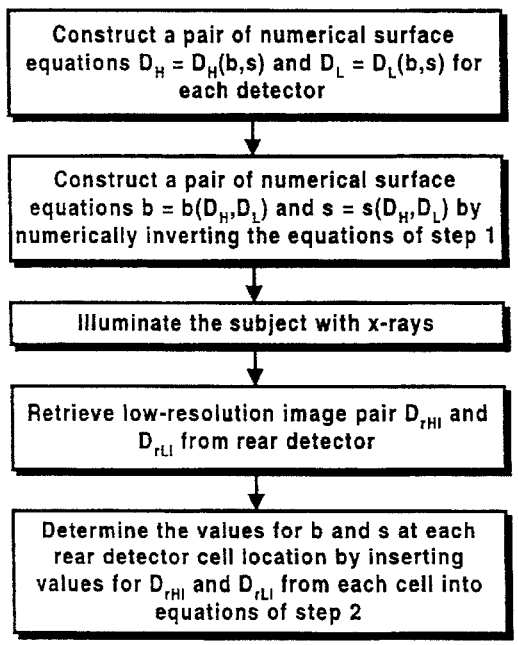
FIG. 3 is a flow diagram of the basic dual-energy data decomposition method using the hardware of FIG. 1.

The following is a step-by-step description of the data decomposition method summarized above and shown in FIG. 3.

The first step is to construct the two numerical surface equations $D_L = D_L(b,s)$ and $D_H = D_H(b,s)$ in three-dimensional space. The preferred method to do this is to determine the detection system energy dependent functions and use these functions to calculate the numerical arrays for $D_L$ and $D_H$.

Note that there is a difference between equation pair (19a,19b) and equation pair (16a,16b). If a unified notation is used, the two pairs have the same form. The system energy-dependent function of a detector, denoted sps(E), is defined as $$sps(E) = \Phi_0(E) \times S(E) \quad (20)$$

where $\Phi_0(E)$ is the x-ray energy spectrum emitted from the x-ray source 14 and S(E) is the energy response function of the detector. In the second embodiment, the equation pair (16a,16b) becomes $$sps_H(E) = \Phi_{0H}(E) \times S_f(E) \quad (21a)$$

$$sps_L(E) = \Phi_{0L}(E) \times S_f(E) \quad (21b)$$

and in the third embodiment, the equation pair (19a,19b) becomes $$sps_H(E) = \Phi_0(E) \times S_{fH}(E) \quad (22a)$$

$$sps_L(E) = \Phi_0(E) \times S_{fL}(E) \quad (22b)$$

The function sps(E) contains the complete energy-related features of the dual-energy imaging system. The advantage of determining sps(E) is that all subsequent data processing methods are made independent of the subject 12.

The preferred method for determining the energy dependent function sps(E) of the image system is the well-established absorption method, which is described in detail in Benjamin R. Archer & Louis K. Wagner, *A Laplace Transform Pair Model for Spectral Reconstruction*, 9 Medical Physics 844 (November/December 1982). Detector absorption curves are measured by using a collimated narrow x-ray beam. An absorption plate composed of a known material, such as aluminum, lucite or copper, is placed between the x-ray source and the detector. The electrical signal from the detector as a function of the absorption plate thickness is experimentally determined by the equation $$D(t) = \int sps(E) \times \exp(-\mu(E) \times t) dE \qquad (23)$$

The electrical signal from a single detector cell D(t) is measured while varying the thickness t of the absorption plate. Since the mass absorption coefficient $\mu(E)$ of the absorption plate material is well known, the function sps(E) can be determined to the accuracy required by the dual-energy x-ray imaging. By using standard least square parameter fitting techniques, the energy dependent function sps(E) can be obtained to a high degree of accuracy for the single cell. For each two-dimensional detector, the energy dependent function sps(E) of one cell can represent all the cells of that detector.

Once the value for sps(E) is determined to the desired accuracy, the dual-energy signals as a function of the material composition of the subject can be calculated through from the equations $$D_H = \int sps_H(E) \times \exp(-(\mu_b(E) \times b + \mu_s(E) \times s)) dE \qquad (24a)$$

and $$D_L = \int sps_L(E) \times \exp(-(\mu_b(E) \times b + \mu_s(E) \times s)) dE \qquad (24b)$$

where $\mu_b(E)$ and $\mu_s(E)$ are the well-documented mass absorption coefficients for bone tissue and soft tissue, respectively. The mass surface densities b and s are assigned values that sufficiently cover the real range of the subject 12.

The second step to obtaining the material composition images b and s from the image pair $D_H$, $D_L$ is to determine $b(D_H, D_L)$ and $S(D_H, D_L)$, as shown graphically in FIGS. 11a to 11d. To do so, the simultaneous equation pair (24a, 24b) must be inverted. A preferred method of inversion is as follows: (1) as in FIGS. 11a and 11b, assign a pair of values in the desired range to b and s corresponding to one of the coordinate points in the (b,s) plane so that $b=b_n$, and $s=s_m$, and, from the two numeric tables representing the three-dimensional surfaces $D_H(b,s)$ and $D_L(b,s)$, determine a pair of $D_H$ and $D_L$ values so that $D_H[n,m]=D_H(b=b_n, s=s_m)$ and $D_L[n,m]=D_L(b=b_n, s=s_m)$, where $D_H[n,m]$ and $D_L[n,m]$ are two specific numbers, and (2) as in FIGS. 11c and 11d, replot the four numbers $D_H[n,m]$, $D_L[n,m]$, $b_n$, and $s_m$ to provide a pair of data points on the three-dimensional surfaces $b(D_H,D_L)$ and $s(D_H,D_L)$. The data point on the three-dimensional surface $b(D_H,D_L)$ is $D_H=D_H[n,m]$, $D_L=D_L[n,m]$, $b=b_n$ and the data point on the three-dimensional surface $s(D_H,D_L)$ is $D_H=D_H[n,m]$, $D_L=D_L[n,m]$, $s=s_m$. This inversion process works because the dual-energy fundamental equation is continuous, smooth, and monotonous in relation to the both variables b and s.

The third step is to determine the desired values for b and s at each discrete cell location by inserting the available data pair $(D_H, D_L)$ into the numerical equations of step 2, or determining the desired values for $D_H$, $D_L$, or only one of them, at each discrete cell location by inserting the available data pair (b,s) into the numerical equations of step 1.

The final step is to maintain the accuracy of the values for b and s to be continuous. Because of the nature of digital computers, the data arrays stored in computer must have finite steps, which are assumed here to be integer values. To eliminate the error in connection with these finite steps in data processing, the difference between the real number and the integer number is recorded in special supplementary data arrays for each calculated value. To do this, the notation is changed. All previous arrays are denoted with a subscript '0' to represent integer results. In step 2, two addition arrays $\delta D_H$ and $\delta D_L$ as functions of $(b_0, s_0)$ are constructed. Previously, in the integer number equation systems, the calculated real numbers $D_H(b_0, s_0)$ and $D_L(b_0, s_0)$ were rounded to become $D_{H0}(b_0, s_0)$ and $D_{L0}(b_0, s_0)$; in the real number equations, to maintain accuracy, the difference between the real numbers and integers is stored in two additional arrays $\delta D_H(b_0, s_0)$ and $\delta D_L(b_0, s_0)$:

$$\delta D_H(b_0, s_0) = D_H(b_0, s_0) - D_{H0}(b_0, s_0)) \qquad (25a)$$

and $$\delta D_L(b_0, s_0) = D_L(b_0, s_0) - D_{L0}(b_0, s_0)) \qquad (25b)$$

where $b_0$, $s_0$, $D_{H0}$, and $D_{L0}$ denote the integer parts of b, s, $D_H$, and $D_L$, respectively.

Then in step 3, for each measured real number pair $(D_H, D_L)$, first use the integer part $(D_{H0}, D_{L0})$ to determine $(b_0, s_0)$ and extend it to the continuous domain by the following equations:

$$\begin{aligned}b = \;& b_0(D_{H0}, D_{L0}) + [\partial b_0(D_{H0}, D_{L0})/\partial D_{L0}] \times [D_L - \\ & \partial D_{L0}(b_0, s_0)] + [\partial b_0(D_{H0}, D_{L0})/\partial D_{H0}] \times [D_H - \\ & \partial D_{H0}(b_0, s_0)] + \text{higher order terms}\end{aligned} \qquad (26a)$$

and $$\begin{aligned}s = \;& s_0(D_{H0}, D_{L0}) + [\partial s_0(D_{H0}, D_{L0})/\partial D_{L0}] \times [D_L - \\ & \partial D_{L0}(b_0, s_0)] + [\partial s_0(D_{H0}, D_{L0})/\partial D_{H0}] \times [D_H - \\ & \partial D_{H0}(b_0, s_0)] + \text{higher order terms}\end{aligned} \qquad (26b)$$

where the higher order terms can be found in standard calculus textbooks.

There are several alternatives to the data decomposition method:

(1) According to current theory, within the energy range of diagnostic x-rays, any two materials with different mass absorption coefficients can be used to represent the x-ray absorption of the human body composition.

(2) The signal pair $(D_H, D_L)$ or signal D can be directly measured at a sufficiently large number of grid (b,s) values, then two dimensional mathematical interpolation methods can be used to obtain the $D_H=D_H(b,s)$ and $D_L=D_L(b,s)$ surfaces.

(3) The entire process may be carried out using a functional scale or grid steps other than linear, such as a logarithmic scale.

(4) Some well-established computation tools such as sorting algorithms or database procedures, can be used to help the inversion process described above.

(5) All currently known dual-energy x-ray data decomposition methods can be used for obtaining the low-resolution front detector imager $D_{fPI}$ or image pair $D_{fHPI}$ and $D_{fLP}$. These methods can be characterized as solving the fundamental dual-energy x-ray equations with continuous energy spectra through first-order approximation (linear approximation) or second-order approximation instead of maintaining the continuous energy spectra.

(6) All the steps described above, including the data decomposition method and the scatter elimination method, can be combined together in various degrees, from combining any two steps to combining all the steps into one procedure. For example, equation pair (18a,18b) and equation pair (17a,17b) can be combined, with minor modifications, into a larger four-equation system and solved using the previously determined $(D_{rH}, D_{rL})$ to find $(D_{fHP}, D_{fLP})$ without explicitly determining (b,s). One way of doing this is to construct a pair of quantitative relationships $D_{fHP}=(D_{rH}, D_{rL})$ and $D_{fLP}=(D_{rH}, D_{rL})$ in a data base and storing them. From the measured data pair $(D_{rH}, D_{rL})$ of the rear detector assembly, a new data pair $(D_{fHP}, D_{fLP})$ of the front detector assembly can be found. Any such method combinations are contemplated by the present invention.

The foregoing description of the preferred embodiments of the invention has been presented for the purpose of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A two-dimensional x-ray imaging system for taking images of a subject, said system comprising:

(a) in physical sequence from front to back, an x-ray source, a front two-dimensional x-ray detector assembly, a collimator, and a rear two-dimensional x-ray detector assembly, said subject being located between said x-ray source and said front detector assembly;

(b) said x-ray source adapted to emit x-rays for passage through said subject;

(c) said x-rays including primary x-rays having their direction of travel unaltered by interaction with said subject;

(d) said x-rays including scatter x-rays having their direction of travel altered by interaction with said subject;

(e) said front detector assembly receiving said primary x-rays and said scatter x-rays;

(f) said collimator being adjacent to said front detector assembly, said collimator permitting the passage of a portion of said primary x-rays and blocking the passage of the remainder of said primary x-rays and said scatter x-rays; and (g) said rear detector assembly being adjacent to said collimator, said rear detector receiving only said portion of said primary x-rays passing through said collimator.

2. The x-ray imaging system of claim 1 wherein said x-ray source emits x-rays with an energy in the range of from approximately 10 keV to approximately 500 keV.

3. The x-ray imaging system of claim 1 wherein said front detector assembly includes a plurality of detector cells arranged in a substantially square matrix with from 32 to 8192 cells on a side.

4. The x-ray imaging system of claim 1 wherein said collimator is composed substantially of an x-ray-absorbent material having a large number of through holes, the axes of said holes being parallel to said direction of travel of said primary x-rays.

5. The x-ray imaging system of claim 4 wherein the thickness of said collimator is between approximately 1 cm and 10 cm.

6. The x-ray imaging system of claim 4 wherein said collimator holes have a substantially round cross-section with a diameter between approximately 0.5 mm and approximately 10 mm and a pitch of between approximately 5 mm and 50 mm.

7. The x-ray imaging system of claim 4 wherein said collimator holes have a substantially square cross-section with a dimension between approximately 0.5 mm and approximately 10 mm and a pitch of between approximately 5 mm and 50 mm.

8. The x-ray imaging system of claim 1 wherein said rear detector assembly includes a rear detector array having a plurality of detector cells arranged in a substantially square matrix with from 32 to 8192 cells on a side and said x-ray source emits two x-ray pulses of differing energies, one of said pulses being in the range of from 10 keV to 100 keV and the other of said pulses being in the range of from 30 keV to 500 keV.

9. The x-ray imaging system of claim 1 wherein said rear detector assembly includes, in physical sequence, a rear low-energy detector, a rear x-ray energy spectral filter, and a rear high-energy detector.

10. The x-ray imaging system of claim 9 wherein said rear low-energy detector includes a plurality of detector cells arranged in a substantially square matrix with from 32 to 8192 cells on a side, said rear high-energy detector includes a plurality of detector cells, the arrangement and quantity of said rear high-energy detector cells being substantially the same as the arrangement and quantity of said rear low-energy detector cells.

11. The x-ray imaging system of claim 9 wherein said front detector assembly includes, in physical sequence, a front low-energy detector, a front x-ray energy spectral filter, and a front high-energy detector.

12. The x-ray imaging system of claim 11 wherein said front low-energy detector includes a plurality of detector cells arranged in a substantially square matrix with from 32 to 8192 cells on a side, said front high-energy detector includes a plurality of detector cells, the arrangement and quantity of said front high-energy detector cells being substantially the same as the arrangement and quantity of said front low-energy detector cells.

13. A two-dimensional x-ray imaging system for taking images of a subject, said system comprising:

(a) in physical sequence from front to back, an x-ray source, a front two-dimensional x-ray detector assembly, a collimator, and a rear two-dimensional x-ray detector assembly, said subject being located between said x-ray source and said front detector assembly;

(b) said x-ray source adapted to emit x-rays with an energy in the range of from approximately 20 keV to approximately 100 key for passage through said subject;

(c) said x-rays including primary x-rays having their direction of travel unaltered by interaction with said subject;

(d) said x-rays including scatter x-rays having their direction of travel altered by interaction with said subject;

(e) said front detector assembly receiving said primary x-rays and said scatter x-rays;

(f) said collimator being adjacent to said front detector assembly, said collimator permitting the passage of a portion of said primary x-rays and blocking the passage of the remainder of said primary x-rays and said scatter x-rays, collimator being composed substantially of an x-ray-absorbent material having a large number of through holes, the axes of said holes being parallel to said direction of travel of said primary x-rays, said collimator holes having a pitch of between approximately 5 mm and 50 mm;

(g) said rear detector assembly being adjacent to said collimator, said rear detector receiving only said portion of said primary x-rays passing through said collimator.

14. The x-ray imaging system of claim 13 wherein said front detector assembly includes a plurality of front detector cells arranged in a substantially square matrix with from 32 to 8192 cells on a side, said rear detector assembly includes a rear detector array having a plurality of rear detector cells arranged in a substantially square matrix with from 32 to 8192 cells on a side, and said x-ray source emits two x-ray pulses of different energies, one of said energies being in the range of from 10 to 100 keV and the other of said energies being in the range of from 30 keV to 500 keV.

15. The x-ray imaging system of claim 13 wherein said front detector assembly includes a plurality of detector cells arranged in a substantially square matrix with from 32 to 8192 cells on a side and said rear detector assembly includes, in physical sequence, a rear low-energy detector, a rear x-ray energy spectral filter, and a rear high-energy detector, said rear low-energy detector including a plurality of rear low-energy detector cells arranged in a substantially square matrix with from 32 to 8192 cells on a side and said rear high-energy detector including a plurality of rear high-energy detector cells, the arrangement and quantity of said rear high-energy detector cells being the same as the arrangement and quantity of said rear low-energy detector cells.

16. The x-ray imaging system of claim 15 wherein said front detector assembly includes, in physical sequence, a front low-energy detector, a front x-ray energy spectral filter, and a front high-energy detector, said front low-energy detector including a plurality of front low-energy detector cells arranged in a substantially square matrix with from 32 to 8192 cells on a side and said front high-energy detector including a plurality of front high-energy detector cells, the arrangement and quantity of said front high-energy detector cells being the same as the arrangement and quantity of said front low-energy detector cells.

17. The x-ray imaging system of claim 13 wherein said collimator holes have a substantially round cross-section with a diameter between approximately 0.5 mm and approximately 10 mm.

18. The x-ray imaging system of claim 13 wherein said collimator holes have a substantially square cross-section with a dimension between approximately 0.5 mm and approximately 10 mm.

19. A method for taking a two-dimensional x-ray image of a subject using a two-dimensional x-ray imaging system, said system including, in physical sequence from front to back, an x-ray source emitting x-rays, a front two-dimensional x-ray detector having a plurality of front detector cells on a coordinate system represented by the notation (x,y), a collimator having a plurality of through holes axially aligned with said x-rays and permitting the passage of a portion of primary x-rays and blocking substantially all scatter x-rays, a rear low-energy two-dimensional x-ray detector having a plurality of rear low-energy detector cells on a coordinate system represented by the notation (i,j), a rear x-ray energy spectral filter, and a rear high-energy two-dimensional x-ray detector having a plurality of rear high-energy detector cells on the same coordinate system as said rear low-energy detector cells, a plurality of projection lines extending radially from said x-ray source through said collimator holes, said subject being substantially composed of two different materials having area densities of A and B in terms of interaction with said x-rays and being located between said x-ray source and said front detector, said method comprising:

(a) illuminating said subject with said x-rays;

(b) retrieving a high-resolution image $I_{fh}$ from substantially all of said front detector cells and processing said image $I_{fh}$ to normalize it and to subtract dark signals, yielding an image $D_{fh}$, which is composed of primary x-ray signals and scatter x-ray signals;

(c) constructing a low-resolution image $D_{fl}$ from the portion of said image $D_{fh}$ retrieved from said front detector cells that are intersected by said projection lines;

(d) retrieving a low-resolution image $I_{rHl}$ from said rear high-energy detector cells that are intersected by said projection lines and processing said image $I_{rHl}$ to normalize it and to subtract dark signals, yielding an image $D_{rHl}$, said image $D_{rHl}$ being composed of substantially only primary x-ray signals;

(e) retrieving a low-resolution image $I_{rLl}$ from said rear low-energy detector cells that are intersected by said projection lines and processing said image $I_{rLl}$ to normalize it and to subtract dark signals, yielding an image $D_{rLl}$, said image $D_{rLl}$ being composed of substantially only primary x-ray signals;

(f) calculating a low-resolution primary x-ray image $D_{fPl}$ of said front detector from a low-resolution dual-energy primary x-ray imaging pair composed of said image $D_{rHl}$ and said image $D_{rLl}$;

(g) calculating a low-resolution scatter x-ray image $D_{fSl}$ of said front detector by subtracting said image $D_{fPl}$ from said image $D_{fl}$;

(h) calculating a high-resolution scatter image $D_{fSh}$ by extending said low-resolution scatter image $D_{fSl}$ to the entire image area of said front detector through interpolation; and (i) calculating a high-resolution primary image $D_{fPh}$ by subtracting said high-resolution scatter image $D_{fSh}$ from said high-resolution image $D_{fh}$;

(j) whereby said high-resolution primary image $D_{fPh}$ is a two-dimensional image of said subject at said front detector after scatter x-rays have been substantially eliminated, said image $D_{fPh}$ having a spatial resolution as high as said front detector can provide.

20. The two-dimensional x-ray image method of claim 19 wherein said low-resolution primary image of said front detector $D_{fPl}$ is calculated by:

(a) solving said low-resolution dual-energy primary x-ray imaging pair from said rear detector for said area densities A and B, wherein $D_{rHl}(i,j)=\int[\Phi_0(E)\times\exp(-(\mu_A(E)\times A(i,j)+\mu_B(E)\times B(i,j)))]\times S_{rH}(E)dE$ and $D_{rLl}(i,j)=\int[\Phi_0(E)\times\exp(-(\mu_A(E)\times A(i,j)+\mu_B(E)\times B(i,j)))]\times S_{rL}(E)dE$; and (b) inserting said A and B solutions into the equation for said image $D_{fPl}(x(i),y(j))=\int[\Phi_0(E)\times S_f(E)]\times\exp(-(\mu_A(E)\times A(i,j)+\mu_B(E)\times B(i,j)))dE$, wherein $(x(i),y(j))$ is the coordinate of said front detector cell intersected by said projection line that also intersects said rear high-energy detector cell (i,j) and said rear low-energy detector cell (i,j), $\Phi_0(E)$ is the energy spectrum of said x-rays, $\mu_A(E)$ is the mass absorption coefficient of said material having area density A, $\mu_B(E)$ is the mass absorption coefficient of said material having area density B, and $S_f(E)$ is the spectral sensitivity of said front detector.

21. The two-dimensional x-ray image method of claim 19 wherein said low-resolution image $D_{fPl}$ is calculated by combining a process for solving said low-resolution dual-energy primary x-ray imaging pair $D_{rHl}$, $D_{rLl}$ from said rear detector for said area densities A and B and the equation for said low-resolution image $D_{fPl}=\int[\Phi_0(E)\times S_f(E)]\times\exp(-(\mu_A(E)\times A(i,j)+\mu_B(E)\times B(i,j)))dE$ into one process using a direct quantitative relationship $D_{fPl}(x(i),y(j))=D_{fPl}(D_{rL}(i,j),D_{rH}(i,j))$, wherein $(x(i),y(j))$ is the coordinate of said front detector cell intersected by said projection line that also intersects said rear high-energy detector cell (i,j).

22. The two-dimensional x-ray image method of claim 19 wherein said low-resolution image $D_{fPl}$ is obtained from said image pair $D_{rLl}(i,j),D_{rHl}(i,j))$ by using linear approximation.

23. The two-dimensional x-ray image method of claim 18 wherein said low-resolution image $D_{fPl}$ is obtained from said image pair $D_{rLl}(i,j),D_{rHl}(i,j))$ by using second order approximation methods.

24. A method for taking a two-dimensional x-ray image of a subject using a two-dimensional x-ray imaging system, said system including, in physical sequence from front to back, an x-ray source emitting x-rays, a front two-dimensional x-ray detector having a plurality of front detector cells on a coordinate system represented by the notation $(x,y)$, a collimator having a plurality of through holes axially aligned with said x-rays and permitting the passage of a portion of primary x-rays and blocking substantially all scatter x-rays, a rear two-dimensional x-ray detector having a plurality of rear detector cells on a coordinate system represented by the notation $(i,j)$, a plurality of projection lines extending radially from said x-ray source through said collimator holes, said subject being substantially composed of two different materials having area densities of A and B in terms of interaction with said x-rays and being located between said x-ray source and said front detector, said method comprising:

(a) illuminating said subject with x-rays of energy level H;

(b) retrieving a high-resolution image $I_{fHh}$ from substantially all of said front detector cells and processing said image $I_{fHh}$ to normalize it and to subtract dark signals, yielding an image $D_{fHh}$, which is composed of primary x-ray signals and scatter x-ray signals;

(c) constructing a low-resolution image $D_{fHl}$ from the portion of said image $D_{fHh}$ retrieved from said front detector cells that are intersected by said projection lines;

(d) retrieving a low-resolution image $I_{rHl}$ from said rear detector cells that are intersected by said projection lines and processing said image $I_{rHl}$ to normalize it and to subtract dark signals, yielding an image $D_{rHl}$, said image $D_{rHl}$ being composed of substantially only primary x-ray signals;

(e) illuminating said subject with x-rays of energy level L;

(f) retrieving a high-resolution image $I_{fLh}$ from substantially all of said front detector cells and processing said image $I_{fLh}$ to normalize it and to subtract dark signals, yielding an image $D_{fLh}$, which is composed of primary x-ray signals and scatter x-ray signals;

(g) constructing a low-resolution image $D_{fLl}$ from the portion of said image $D_{fLh}$ retrieved from said front detector cells that are intersected by said projection lines;

(h) retrieving a low-resolution image $I_{rLl}$ from said rear detector cells that are intersected by said projection lines and processing said image $I_{rLl}$ to normalize it and to subtract dark signals, yielding an image $D_{rLl}$, said image $D_{rLl}$ being composed of substantially only primary x-ray signals;

(i) calculating a pair of low-resolution primary x-ray images $D_{fLPl}$ and $D_{fHPl}$ of said front detector from a low-resolution dual-energy primary x-ray imaging pair composed of said image $D_{rHl}$ and said image $D_{rLl}$;

(j) calculating a pair of low-resolution scatter x-ray images $D_{fLSl}$ and $D_{fHSl}$ of said front detector by subtracting said image $D_{fLPl}$ from said image $D_{fLl}$ and subtracting said image $D_{fHPl}$ from said image $D_{fHl}$;

(k) calculating a pair of high-resolution scatter images $D_{fLSh}$ and $D_{fHSh}$ by extending said pair of low-resolution scatter images $D_{fLSl}$ and $D_{fHSl}$ to the entire image area of said front detector through interpolation; and (l) calculating a pair of high-resolution primary images $D_{fLPh}$ and $D_{fHPh}$ by subtracting said high-resolution scatter image $D_{fLSh}$ from said high-resolution image $D_{fLh}$ and subtracting said high-resolution scatter image $D_{fHSh}$ from said high-resolution image $D_{fHh}$;

(m) whereby said pair of high-resolution primary images $D_{fLPh}$ and $D_{fHPh}$ is a pair of high-resolution two-dimensional dual-energy x-ray images of said subject at said front detector after scatter x-rays have been substantially eliminated, said primary image pair $D_{fLPh}$ and $D_{fHPh}$ having a spatial resolution as high as said front detector can provide.

25. The two-dimensional x-ray image method of claim 24 wherein said area densities A and B are calculated from said pair of high-resolution primary images $D_{fLPh}$ and $D_{fHPh}$, said material compositions having a resolution as high as said front detector can provide.

26. The two-dimensional x-ray image method of claim 24 wherein said pair of low-resolution images of said front detector $D_{fHPl}$ and $D_{fLPl}$ are calculated by:

(a) solving said low-resolution dual-energy primary x-ray imaging pair for said area densities A and B, wherein $D_{rHl}(i,j)=\int[\Phi_{OH}(E)\times\exp(-(\mu_A(E)\times A(i,j)+\mu_B(E)\times B(i,j)))]\times S_r(E)dE$ and $D_{rLl}(i,j)=\int[\Phi_{OL}(E)\times\exp(-(\mu_A(E)\times A(i,j)+\mu_B(E)\times B(i,j)))]\times S_r(E)dE$; and (b) inserting said A and B solutions into the equations for said image pair $D_{fLPl}(x(i),y(j))=\int[\Phi_{OL}(E)\times S_f(E)]\times\exp(-(\mu_A(E)\times A(i,j)+\mu_B(E)\times B(i,j)))dE$ and $D_{fHPl}(x(i),y(j))=\int[\Phi_{OH}(E)\times S_f(E)]\times\exp(-(\mu_A(E)\times A(i,j)+\mu_B(E)\times B(i,j)))dE$, wherein $(x(i),y(j))$ is the coordinate of said front detector cell intersected by said projection line that also intersects said rear detector cell $(i,j)$, $\Phi_{OL}(E)$ is the energy spectrum of said x-rays of energy L, $\Phi_{OH}(E)$ is the energy spectrum of said x-rays of energy H, $\mu_A(E)$ is the mass absorption coefficient of said material having area density A, $\mu_B(E)$ is the mass absorption coefficient of said material having area density B, and $S_f(E)$ is the spectral sensitivity of said front detector.

27. The two-dimensional x-ray image method of claim 24 wherein said low-resolution image pair $D_{fLPl}$, $D_{fHPl}$ is calculated by combining a process for solving said low-resolution dual-energy primary x-ray image pair $D_{rHl}$, $D_{rLl}$ for said having area densities A and B and the equation pair for said low-resolution image pair $D_{fHPl}(x(i),y(j))=\int[\Phi_{OH}(E)\times S_f(E)]\times\exp(-(\mu_A(E)\times A(i,j)+\mu_B(E)\times B(i,j)))dE$, $D_{fLPl}(x(i),y(j))=\int[\Phi_{OL}(E)\times S_f(E)]\times\exp((-(\mu_A(E)\times A(i,j)+\mu_B(E)\times B(i,j)))dE$ into one process using direct quantitative relationships $D_{fHPl}(x(i),y(j))=D_{fHPl}(D_{rL}(i,j),D_{rH}(i,j))$ and $D_{fLPl}(x(i),y(j))=D_{fHPl}(D_{rL}(i,j),D_{rH}(i,j))$, wherein $(x(i),y(j))$ is the coordinate of said front detector cell intersected by said projection line that also intersects said rear high-energy detector cell $(i,j)$.

28. The two-dimensional x-ray image method of claim 24 wherein said low-resolution image pair $D_{fHPl}$ and $D_{fLPl}$ is obtained from said image pair $D_{rL}(i,j),D_{rH}(i,j))$ by using linear approximation.

29. The two-dimensional x-ray image method of claim 24 wherein said low-resolution image pair $D_{fHPl}$ and $D_{fLPl}$ is obtained from said image pair $D_{rL}(i,j),D_{rH}(i,j))$ by using second order approximation methods.

30. A method for taking a two-dimensional x-ray image of a subject using a two-dimensional x-ray imaging system, said system including, in physical sequence from front to back, an x-ray source emitting x-rays, a front low-energy two-dimensional x-ray detector having a plurality of front low-energy detector cells on a coordinate system represented by the notation (x,y), a front x-ray energy spectral filter, a front high-energy two-dimensional x-ray detector having a plurality of front high-energy detector cells on the same coordinate system as said front low-energy detector cells, a collimator having a plurality of through holes axially aligned with said x-rays and permitting the passage of a portion of primary x-rays and blocking substantially all scatter x-rays, a rear low-energy two-dimensional x-ray detector having a plurality of rear low-energy detector cells on a coordinate system represented by the notation (i,j), a rear x-ray energy spectral filter, and a rear high-energy two-dimensional x-ray detector having a plurality of rear high-energy detector cells on the same coordinate system as said rear low-energy detector cells, a plurality of projection lines extending radially from said x-ray source through said collimator holes, said subject being substantially composed of two different materials having area densities of A and B in terms of interaction with said x-rays and being located between said x-ray source and said front detector, said method comprising:

(a) illuminating said subject with x-rays;

(b) retrieving a high-resolution image $I_{fLh}$ from substantially all of said front low-energy detector cells and processing said image $I_{fLh}$ to normalize it and to subtract dark signals, yielding an image $D_{fLh}$, which is composed of primary x-ray signals and scatter x-ray signals;

(c) constructing a low-resolution image $D_{fLl}$ from the portion of said image $D_{fLh}$ retrieved from said front low-energy detector cells that are intersected by said projection lines;

(d) retrieving a high-resolution image $I_{fHh}$ from substantially all of said front high-energy detector cells and processing said image $I_{fHh}$ to normalize it and to subtract dark signals, yielding an image $D_{fHh}$, which is composed of primary x-ray signals and scatter x-ray signals;

(e) constructing a low-resolution image $D_{fHl}$ from the portion of said image $D_{fHh}$ retrieved from said front high-energy detector cells that are intersected by said projection lines;

(f) retrieving a low-resolution image $I_{rLl}$ from said rear low-energy detector cells that are intersected by said projection lines and processing said image $I_{rLl}$ to normalize it and to subtract dark signals, yielding an image $D_{rLl}$, said image $D_{rLl}$ being composed of substantially only primary x-ray signals;

(g) retrieving a low-resolution image $I_{rHl}$ from said rear high-energy detector cells that are intersected by said projection lines and processing said image $I_{rHl}$ to normalize it and to subtract dark signals, yielding an image $D_{rHl}$, said image $D_{rHl}$ being composed of substantially only primary x-ray signals;

(h) calculating a pair of low-resolution primary x-ray images $D_{fLPl}$ of said front low-energy detector and $D_{fHPl}$ of said front high-energy detector from a low-resolution dual-energy primary x-ray imaging pair composed of said image $D_{rHl}$ and said image $D_{rLl}$;

(j) calculating a pair of low-resolution scatter x-ray images $D_{fLSl}$ of said front low-energy detector and $D_{fHSl}$ of said front high-energy detector by subtracting said image $D_{fLPl}$ from said image $D_{fLl}$ and subtracting said image $D_{fHPl}$ from said image $D_{fHl}$;

(k) calculating a pair of high-resolution scatter images $D_{fLSh}$ and $D_{fHSh}$ by extending said pair of low-resolution scatter images $D_{fLSl}$ and $D_{fHSl}$ to the entire image area of said front low-energy detector and said front high-energy detector through interpolation; and (l) calculating a pair of high-resolution primary images $D_{fLPh}$ and $D_{fHPh}$ by subtracting said high-resolution scatter image $D_{fLSh}$ from said high-resolution image $D_{fLh}$ and subtracting said high-resolution scatter image $D_{fHSh}$ from said high-resolution image $D_{fHh}$;

(m) whereby said pair of high-resolution primary images $D_{fLPh}$ and $D_{fHPh}$ is a pair of high-resolution two-dimensional dual-energy x-ray images of said subject at said front low-energy detector and said front high-energy detector after scatter x-rays have been substantially eliminated, said primary image pair $D_{fLPh}$ and $D_{fHPh}$ having a spatial resolution as high as said front detector can provide.

31. The two-dimensional x-ray image method of claim 30 wherein said area densities A and B are calculated from said pair of high-resolution primary images $D_{fLPh}$ and $D_{fHPh}$, said material compositions having a resolution as high as said front detectors can provide.

32. The two-dimensional x-ray image method of claim 30 wherein said pair of low-resolution images of said front detector $D_{fLPl}$ and $D_{fHPl}$ are calculated by:

(a) solving said low-resolution dual-energy primary x-ray imaging pair for said area densities A and B; and (b) inserting said A and B solutions into the equations for said image pair $D_{fLPl}(x(i),y(j))=\int[\Phi_0(E)\times S_{fL}(E)]\times\exp(-(\mu_A(E)\times A(i,j)+\mu_B(E)\times B(i,j)))dE$ and $D_{fHPl}(x(i),y(j))=\int[\Phi_0(E)\times S_{fH}(E)]\times\exp(-(\mu_A(E)\times A(i,j)+\mu_B(E)\times B(i,j)))dE$, wherein $(x(i),y(j))$ is the coordinate of said front low-energy detector cell and said front high-energy detector cell intersected by said projection line that also intersects said rear high-energy detector cell $(i,j)$ and said rear low-energy detector cell $(i,j)$, $\Phi_0(E)$ is the energy spectrum of said x-rays, $S_{fL}(E)$ is the spectral sensitivity of said front low-energy detector, $S_{fH}(E)$ is the spectral sensitivity of said front high-energy detector, $\mu_A(E)$ is the mass absorption coefficient of said material having area density A, and $\mu_B(E)$ is the mass absorption coefficient of said material having area density B.

33. The two-dimensional x-ray image method of claim 30 wherein said low-resolution image pair $D_{fLPl}$, $D_{fHPl}$ is calculated by combining a process for solving said low-resolution dual-energy primary x-ray image pair $D_{rHl}$, $D_{rLl}$ for said having area densities A and B and the equation pair for said low-resolution image pair $D_{fHPl}(x(i),y(j))=\int[\Phi_0(E)\times S_{fH}(E)]\times\exp(-(\mu_A(E)\times A(i,j)+\mu_B(E)\times B(i,j)))dE$, $D_{fLPl}(x(i),y(j))=\int[\Phi_0(E)\times S_{fL}(E)]\times\exp((-(\mu_A(E)\times A(i,j)+\mu_B(E)\times B(i,j)))dE$ into one process using direct quantitative relationships $D_{fHPl}(x(i),y(j))=D_{fHPl}(D_{rL}(i,j),D_{rH}(i,j))$ and $D_{fLPl}(x(i),y(j))=D_{fHPl}(D_{rL}(i,j),D_{rH}(i,j))$, wherein $(x(i),y(j))$ is the coordinate of said front detector cell intersected by said projection line that also intersects said rear high-energy detector cell $(i,j)$.

34. The two-dimensional x-ray image method of claim 30 wherein said low-resolution image pair $D_{fHPl}$ and $D_{fLPl}$ is obtained from said image pair $D_{rLl}(i,j),D_{rHl}(i,j))$ by using linear approximation.

35. The two-dimensional x-ray image method of claim 30 wherein said low-resolution image pair $D_{fHPl}$ and $D_{fLPl}$ is obtained from said image pair $D_{rLl}(i,j),D_{rHl}(i,j))$ by using second order approximation methods.

36. A method for taking a two-dimensional x-ray image of a subject using a two-dimensional x-ray imaging system, said system including, in physical sequence from front to back, an x-ray source emitting x-rays that can be approximated as having a single energy $E_0$, a front two-dimensional x-ray detector having a plurality of front detector cells on a coordinate system represented by the notation $(x,y)$, a collimator having a plurality of through holes axially aligned with said x-rays and permitting the passage of a portion of primary x-rays and blocking substantially all scatter x-rays, a rear two-dimensional x-ray detector having a plurality of rear detector cells on a coordinate system represented by the notation $(i,j)$, a plurality of projection lines extending radially from said x-ray source through said collimator holes, said subject being substantially composed of two different materials having area densities of A and B in terms of interaction with said x-rays and being located between said x-ray source and said front detector, said method comprising:

(a) illuminating said subject with said x-rays;

(b) retrieving a high-resolution image $I_{fh}$ from substantially all of said front detector cells and processing said image $I_{fh}$ to normalize it and to subtract dark signals, yielding an image $D_{fh}$, which is composed of primary x-ray signals and scatter x-ray signals;

(c) constructing a low-resolution image $D_{fl}$ from the portion of said image $D_{fh}$ retrieved from said front detector cells that are intersected by said projection lines;

(d) retrieving a low-resolution image $I_{rl}$ from rear detector cells that are intersected by said projection lines and processing said image $I_{rl}$ to normalize it and to subtract dark signals, yielding an image $D_{rl}$, said image $D_{rl}$ being composed of substantially only primary x-ray signals;

(e) calculating a low-resolution primary x-ray image $D_{fPl}$ of said front detector from said image $D_{rl}$ by multiplying said image $D_{rl}$ by a predetermined value C, the energy reduction constant of said collimator at said energy $E_0$;

(f) calculating a low-resolution scatter x-ray image $D_{fSl}$ of said front detector by subtracting said image $D_{fPl}$ from said image $D_{fl}$;

(g) calculating a high-resolution scatter image $D_{fSh}$ by extending said low-resolution scatter image $D_{fSl}$ to the entire image area of said front detector through interpolation; and (h) calculating a high-resolution primary image $D_{fPh}$ by subtracting said high-resolution scatter image $D_{fSh}$ from said high-resolution image $D_{fh}$;

(i) whereby said high-resolution primary image $D_{fPh}$ is a two-dimensional image of said subject at said front detector after scatter x-rays have been substantially eliminated, said image $D_{fPh}$ having a spatial resolution as high as said front detector can provide.

37. A method for taking a two-dimensional x-ray image of a subject using a two-dimensional x-ray imaging system, said system including, in physical sequence from front to back, an x-ray source emitting x-rays that can be approximated as having an average energy $E_0$, a front two-dimensional x-ray detector having a plurality of front detector cells on a coordinate system represented by the notation $(x,y)$, a collimator having a plurality of through holes axially aligned with said x-rays and permitting the passage of a portion of primary x-rays and blocking substantially all scatter x-rays, a rear two-dimensional x-ray detector having a plurality of rear detector cells on a coordinate system represented by the notation $(i,j)$, a plurality of projection lines extending radially from said x-ray source through said collimator holes, said subject being substantially composed of two different materials having area densities of A and B in terms of interaction with said x-rays and being located between said x-ray source and said front detector, said method comprising:

(a) illuminating said subject with said x-rays;

(b) retrieving a high-resolution image $I_{fh}$ from substantially all of said front detector cells and processing said image $I_{fh}$ to normalize it and to subtract dark signals, yielding an image $D_{fh}$, which is composed of primary x-ray signals and scatter x-ray signals;

(c) constructing a low-resolution image $D_{fl}$ from the portion of said image $D_{fh}$ retrieved from said front detector cells that are intersected by said projection lines;

(d) retrieving a low-resolution image $I_{rl}$ from said rear detector cells that are intersected by said projection lines and processing said image $I_{rl}$ to normalize it and to subtract dark signals, yielding an image $D_{rl}$, said image $D_{rl}$ being composed of substantially only primary x-ray signals;

(e) calculating a low-resolution primary x-ray image $D_{fPl}$ of said front detector from said image $D_{rl}$ by multiplying said image $D_{rl}$ by a predetermined value C, the energy reduction constant of said collimator at said energy $E_0$;

(f) calculating a low-resolution scatter x-ray image $D_{fSl}$ of said front detector by subtracting said image $D_{fPl}$ from said image $D_{fl}$;

(g) calculating a high-resolution scatter image $D_{fSh}$ by extending said low-resolution scatter image $D_{fSl}$ to the entire image area of said front detector through interpolation; and (h) calculating a high-resolution primary image $D_{fPh}$ by subtracting said high-resolution scatter image $D_{fSh}$ from said high-resolution image $D_{fh}$;

(i) whereby said high-resolution primary image $D_{fPh}$ is a two-dimensional image of said subject at said front detector after scatter x-rays have been substantially eliminated, said image $D_{fPh}$ having a spatial resolution as high as said front detector can provide.

* * * * *